(12) United States Patent
Kataoka

(10) Patent No.: US 9,377,348 B2
(45) Date of Patent: Jun. 28, 2016

(54) MEASURING SYSTEM

(71) Applicant: CANON KABUSHIKI KAISHA, Tokyo (JP)

(72) Inventor: Kenichi Kataoka, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 319 days.

(21) Appl. No.: 13/916,128

(22) Filed: Jun. 12, 2013

(65) Prior Publication Data

US 2013/0333477 A1     Dec. 19, 2013

(30) Foreign Application Priority Data

Jun. 15, 2012   (JP) ................................. 2012-135446

(51) Int. Cl.

| | |
|---|---|
| *G01H 9/00* | (2006.01) |
| *A61B 5/055* | (2006.01) |
| *A61B 5/00* | (2006.01) |
| *H02N 2/14* | (2006.01) |
| *A61B 5/04* | (2006.01) |
| *H02N 2/16* | (2006.01) |
| *G01R 33/28* | (2006.01) |

(Continued)

(52) U.S. Cl.
CPC ................ *G01H 9/00* (2013.01); *A61B 5/0051* (2013.01); *A61B 5/055* (2013.01); *A61B 5/7217* (2013.01); *H02N 2/142* (2013.01); *A61B 5/0042* (2013.01); *A61B 5/0046* (2013.01); *A61B 5/04008* (2013.01); *G01R 33/285* (2013.01); *G01R 33/565* (2013.01); *H02N 2/163* (2013.01)

(58) Field of Classification Search
CPC ...... G01H 9/00; A61B 19/2203; A61B 5/055; A61B 5/7217; H02N 2/142
USPC .......................................................... 73/655
See application file for complete search history.

(56) References Cited

U.S. PATENT DOCUMENTS

| | | | | |
|---|---|---|---|---|
| 4,837,512 A | * | 6/1989 | Suzuki | ........................ 324/306 |
| 5,023,553 A | * | 6/1991 | Sano et al. | ..................... 324/309 |

(Continued)

FOREIGN PATENT DOCUMENTS

| | | | |
|---|---|---|---|
| DE | 102010012782 | * | 9/2011 |
| JP | 07-178169 A | | 7/1995 |

(Continued)

OTHER PUBLICATIONS

Basic Contract Accomplishment Report of Research and Development of Miniature Surgical Robotic System Achieving Future Medical Treatment, New Energy and Industrial Technology Development Organization (NEDO), May 19, 2007, Kawasaki, Kanagawa, Japan.

*Primary Examiner* — J M Saint Surin
(74) *Attorney, Agent, or Firm* — Canon USA, Inc. I.P. Division

(57) ABSTRACT

A measuring system for measuring a physical quantity related to one of an electromagnetic wave and a magnetic field includes a vibration-type actuator, a waveform generating unit configured to generate a driving waveform signal of the vibration-type actuator, an optical transmitter unit configured to receive the driving waveform signal and convert the driving waveform signal into an optical signal, an optical receiver unit configured to receive the optical signal and convert the optical signal into an alternating-current voltage signal, and a drive circuit configured to receive the alternating-current voltage signal and apply the alternating-current voltage signal to the vibration-type actuator. The waveform generating unit and the optical transmitter unit are disposed outside a magnetic shield room. The optical receiver unit, the drive circuit, and the vibration-type actuator are disposed inside the magnetic shield room, and the optical signal is transmitted between the optical transmitter unit and the optical receiver unit.

24 Claims, 12 Drawing Sheets

(51) Int. Cl.
*G01R 33/565* (2006.01)

(56) References Cited

U.S. PATENT DOCUMENTS 5,384,573 A * 1/1995 Turpin ............................ 342/179
8,369,037 B2 * 2/2013 Lee ................................ 359/824

FOREIGN PATENT DOCUMENTS

| JP | 07-319543 A | 12/1995 |
| JP | 2003-534859 A | 11/2003 |
| JP | 2006-015045 A | 1/2006 |
| JP | 2008023152 * | 2/2008 |
| JP | 2008-301918 A | 12/2008 |
| JP | 2011-245202 A | 12/2011 |

* cited by examiner

MEASURING SYSTEM

BACKGROUND OF THE INVENTION

1. Field of the Invention

The present disclosure relates to a measuring system and, in particular, to a measuring system for measuring a physical quantity of electromagnetic wave or magnetism in a magnetic shield room.

2. Description of the Related Art

In recent years, much research of medical robotic instruments, such as a manipulator, has been reported. A typical example of a medical robotic instrument is a medical system using a magnetic resonance imaging (MRI) apparatus. In the medical system, an MR image is viewed and the position of a robot arm of a manipulator is controlled in order to diagnose with an accurate biopsy and provide medical treatment. An MRI system is a measuring system in which an electromagnetic wave generated by a static magnetic field and a particular high frequency magnetic field is applied to a part of an examinee (an object to be examined) and, thereafter, by using nuclear magnetic resonance occurring in the object to be examined, an image of the specimen is generated. In this manner, the MRI system acquires information regarding the object to be examined.

Since an MRI system uses a strong magnetic field, it is difficult to use an electromagnetic motor that includes a ferromagnetic material as a power source of a robot arm. Accordingly, a vibration-type actuator, such as an ultrasonic motor, is suitable for the power source. However, since high-frequency noise generated by a control unit of the vibration-type actuator also has an impact on an MR image, the noise generated by the control unit needs to be minimized or shielded. In general, a central processing unit (CPU) or a field programmable gate array (FPGA) that serves as the control unit operates with an external clock of about 10 MHz to about 50 MHz. Accordingly, high-frequency noise generated by the clock signal is transferred to the vibration-type actuator via, for example, a driving waveform signal and, thus, electromagnetic noise is generated around the vibration-type actuator.

Japanese Patent Laid-Open No. 2011-245202 describes a configuration in which the vibration-type actuator is disposed in a cylindrical measuring unit (a bore) of an MRI apparatus while a control unit of the vibration-type actuator is disposed at a position that is the furthest away from the measuring unit of the MRI apparatus placed in a magnetic shield room. In addition, the vibration-type actuator is connected to the control unit using an electromagnetically shielded control line.

Another configuration is described in "Basic Contract Accomplishment Report of Research and Development of Miniature Surgical Robotic System Achieving Future Medical Treatment,", New Energy and Industrial Technology Development Organization. In the configuration, a control unit and a drive circuit of the vibration-type actuator are disposed outside a magnetic shield room and are connected to the vibration-type actuator disposed in the magnetic shield room using a double-shielded electric cable. In addition, a noise filter is provided to part of the cable that passes through a wall of the magnetic shield room to block noise getting into the magnetic shield room. Furthermore, in order to reduce electromagnetic noise generated by an electric current flowing in the vibration-type actuator, the vibration-type actuator is disposed in an aluminum case so as to be electromagnetically shielded.

In Japanese Patent Laid-Open No. 2011-245202, the vibration-type actuator is connected to the control unit using a shielded line. However, since the control unit is disposed in the magnetic shield room, high-frequency radiation noise from the control unit may have an impact on an MR image. In addition, in the technique described in "MRI-compatible Compact Surgical Robot Master-Agreement Research Report", the electric cable extending to the vibration-type actuator is double-shielded, and a connection port connected to the magnetic shield room has a noise filter. However, since the vibration-type actuator is electrically connected to the drive circuit and the control unit, it is difficult to completely block high-frequency noise. Accordingly, if the vibration-type actuator is driven in the vicinity of the MRI apparatus, noise may be coupled into an MR image. In addition, as the length of the interconnection line of the vibration-type actuator increases, the load capacity of the interconnection line increases and, therefore, power consumption may increase.

SUMMARY OF THE INVENTION

Accordingly, the present disclosure provides a measuring system capable of reducing electromagnetic noise transferred from a unit that outputs a driving waveform signal of a vibration-type actuator to the vibration-type actuator.

According to an embodiment disclosed herein, a measuring system for measuring a physical quantity related to one of an electromagnetic wave and a magnetic field includes a vibration-type actuator, a waveform generating unit configured to generate a driving waveform signal of the vibration-type actuator, an optical transmitter unit configured to receive the driving waveform signal and convert the driving waveform signal into an optical signal, an optical receiver unit configured to receive the optical signal and convert the optical signal into an alternating-current voltage signal, and a drive circuit configured to receive the alternating-current voltage signal and output a drive voltage to be applied to the vibration-type actuator.

The waveform generating unit and the optical transmitter unit are disposed outside a magnetic shield room. The optical receiver unit, the drive circuit, and the vibration-type actuator are disposed inside the magnetic shield room, and the optical signal is transmitted between the optical transmitter unit and the optical receiver unit.

According to another embodiment of the present invention, a measuring system for measuring a physical quantity related to one of an electromagnetic wave and a magnetic field includes a vibration-type actuator, a waveform generating unit configured to generate a driving waveform signal of the vibration-type actuator, a first optical transmitter unit configured to receive the driving waveform signal and convert the driving waveform signal into a first optical signal, a first optical receiver unit configured to receive the first optical signal and convert the first optical signal into a first alternating-current voltage signal, a drive circuit configured to receive the first alternating-current voltage signal and apply the first alternating-current voltage signal to the vibration-type actuator, a detecting unit configured to detect a drive state of a driven member that is driven by the vibration-type actuator, a second optical transmitter unit configured to convert a detection signal output from the detecting unit into a second optical signal, a second optical receiver unit configured to receive the second optical signal and convert the second optical signal into a second alternating-current voltage signal, and a control unit configured to control at least one of a frequency, a phase, and an amplitude of the driving waveform signal on the basis of the second alternating-current voltage signal.

The waveform generating unit, the first optical transmitter unit, the second optical receiver unit, and the control unit are disposed outside a magnetic shield room. The first optical receiver unit, the drive circuit, the vibration-type actuator, the detecting unit, and the second optical transmitter unit are disposed inside the magnetic shield room, and the optical signal is transmitted between the first optical transmitter unit and the first optical receiver unit and between the second optical transmitter unit and the second optical receiver unit.

Further features of the present invention will become apparent from the following description of exemplary embodiments with reference to the attached drawings.

DESCRIPTION OF THE EMBODIMENTS

According to an exemplary embodiment of the present disclosure, a measuring system for measuring the physical quantity related to an electromagnetic wave or magnetism can be used in, in particular, a medical system including an MRI apparatus. An MRI apparatus irradiates an object to be examined with radiofrequency pulses. Thereafter, the MRI apparatus receives an electromagnetic wave emitted from the object to be examined by using a highly sensitive receiver coil (an RF coil). Subsequently, the MRI apparatus obtains a magnetic resonance (MR) image of the object to be examined on the basis of a reception signal output from the receiver coil. However, according to the present exemplary embodiment, the measuring system is not limited to be used for medical systems. The present exemplary embodiment is applicable to any measuring system for measuring the physical quantity related to an electromagnetic wave or magnetism (e.g., a magnetic flux density (Tesla: T), a magnetic field strength (A/m), and an electric field strength (V/m)). Exemplary embodiments of the present invention are described below with reference to the accompanying drawings.

First Exemplary Embodiment

Figure 1:
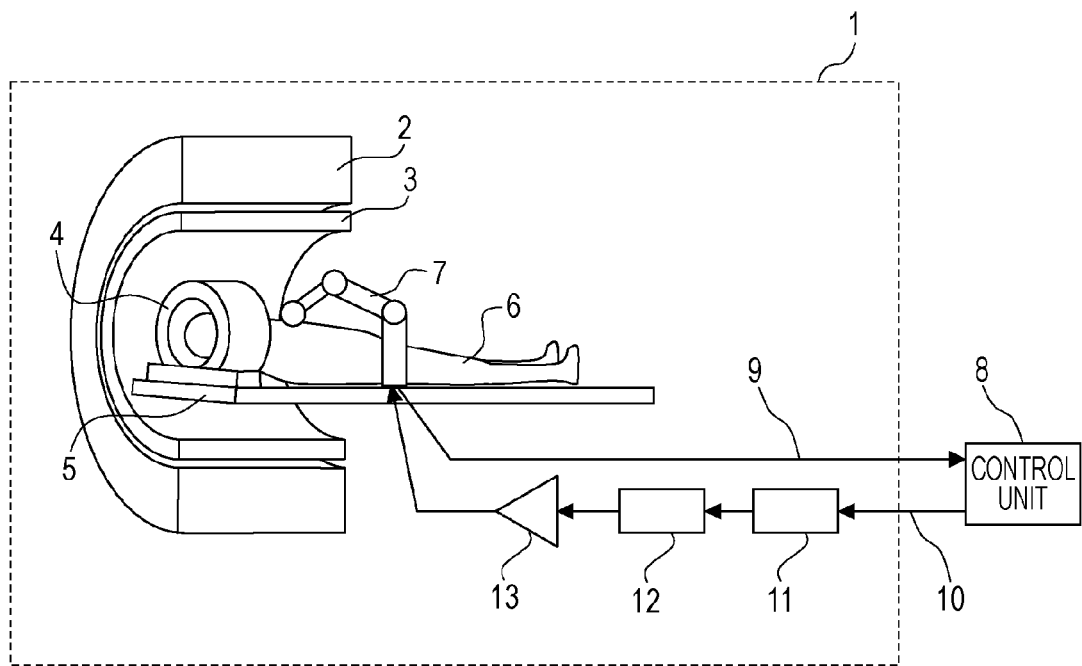
FIG. 1 is a schematic illustration of the configuration of a system according to a first exemplary embodiment.

FIG. 1 is a schematic illustration of an exemplary configuration of a medical care system according to a first exemplary embodiment of the present disclosure. This system performs function magnetic resonance imaging (fMRI). The term "fMRI" refers to a technique for visualizing a change in a blood current caused by the activity of the brain or spine using an MRI apparatus. In this system, a robot arm is moved using a vibration-type actuator to change the contact stimulus in a time-series manner and measures a change in a blood current flowing in the brain. In addition to contact stimulus, a variety of stimuli, such as visual stimulus and auditory stimulus, are attempted to use. In particular, when a robot arm, for example, is moved in the MRI apparatus, electromagnetic noise generated by a drive source is reduced using magnetic shield. In addition, components of the MRI apparatus are demagnetized.

Basic Configuration of MRI Apparatus

The configuration of a system including an MRI apparatus serving as the measuring system of the present exemplary embodiment is described first with reference to FIG. 1. The system according to the present exemplary embodiment includes at least a measuring unit disposed in a magnetic shield room 1 and a control unit 8 disposed outside the magnetic shield room 1.

An MRI apparatus is highly sensitive to electromagnetic noise around a frequency called the Larmor frequency which is determined in accordance with the magnetic field strength unique to the MRI apparatus. The Larmor frequency represents the frequency of the precession of the magnetic dipole moments of atom cores in the brain of an examinee 6. In widely used clinical MRI apparatuses, the magnetic field strength is in the range from 0.2 T to 3 T. At that time, the Larmor frequency is in the range from 8.5 MHz to 128 MHz. A unit that operates in the magnetic shield room needs to minimize the occurrence of electromagnetic noise in such a frequency band. However, in general, the control unit 8 that includes a CPU or an FPGA operates with an external clock in the range from about 10 MHz to about 50 MHz. Thus, unfortunately, electromagnetic noise generated by the clock signal and its higher harmonic wave have a frequency range that widely overlaps the range of the Larmor frequency. Therefore, a measuring unit for measuring a slight change in the magnetic field occurring in the brain is disposed in the magnetic shield room 1 that blocks interference of exogenous noise.

The measuring unit of the MRI apparatus includes at least a superconducting magnet 2 that generates a static magnetic field, a gradient magnetic field generation coil 3 that generates the gradient magnetic field for identifying a three-dimensional position, an RF coil 4 that serves as a receiving unit for irradiating the examinee 6 with an electromagnetic wave and receiving the electromagnetic wave, and a bed 5 for the examinee 6. In reality, each of the superconducting magnet 2 and the gradient magnetic field generation coil 3 is cylindrical in shape. In FIG. 1, each of the superconducting magnet 2 and the gradient magnetic field generation coil 3 is cut into a half. The RF coil 4 is dedicated to measurement for an MR image of the brain. Thus, the RF coil 4 is cylindrical in shape so as to cover the head (an object to be examined) of the examinee 6 who remains lying down on the bed 5. In response to a control signal sent from a controller (not illustrated) disposed outside the magnetic shield room 1, the measuring unit of the MRI apparatus generates a variety of sequences of the gradient magnetic field and irradiates the head with the electromagnetic wave. An external controller (not illustrated) obtains a variety of types of information regarding the brain using a reception signal acquired from the RF coil 4. Note that the controller for controlling the electromagnetic wave may be also incorporated into the control unit 8.

In addition, a robot arm 7 is fixed to the bed 5 in the measuring unit. The robot arm 7 can perform three degree of freedom motion with rotation of two joints and the base portion. The robot arm 7 allows a contact ball attached to the end thereof to touch the examinee 6 at a desired position with a desired pressing force and, thus, can provide time-series stimulus to the examinee 6. Each of the joints and the rotary base portion has the vibration-type actuator illustrated in FIG. 2 and a rotation sensor and a force sensor (not illustrated). The signals output from the rotation sensor and the force sensor are converted into optical signals and are transferred to the control unit 8 disposed outside the magnetic shield room 1 via an optical fiber 9. The robot arm 7 has a mechanism in which the vibration-type actuator is provided to each of the joints, and the vibration-type actuator directly drives the joint. Such a mechanism increases the rigidity of the entire robot arm 7. Thus, the robot arm 7 can operate so as to provide the examinee 6 with a variety of stimuli in a wide frequency range. The main structure of the robot arm 7 (including the vibration-type actuator) is formed of a non-magnetic material. Thus, the design is such that a disturbance of the static magnetic field generated by the superconducting magnet 2 is minimized.

In an actual measurement, the examinee 6 holds the top end of the robot arm 7 by hand and maintains the arm stationary as much as possible. Subsequently, a force is generated by the robot arm 7, and a blood current in the brain of the examinee 6 is measured by changing the strength and the direction of the force in a time-series manner. To perform such a measurement, a force needs to be applied at all times. Accordingly, the robot arm 7 is continuously driven.

The control unit 8 outputs a drive signal (a driving waveform signal) for driving the vibration-type actuator in accordance with the result of comparison of a time-series signal for stimulating the examinee 6 using a predetermined track and a predetermined pressing force and information output from the rotation sensor and the force sensor. The driving waveform signal is a pulse signal obtained by performing pulse width modulation (PWM) on a sine wave. The pulse-width modulated signal is converted into an optical signal by the control unit 8 and is transferred to the inside of the magnetic shield room 1 using an optical fiber 10. That is, according to the present exemplary embodiment, the control unit 8 functions as a waveform generating unit and an optical transmitter unit.

The optical fiber 10 functioning as an optical waveguide unit transmits an optical signal obtained by converting a pulse signal into light. The optical waveguide unit and a modification of the optical waveguide unit are described in more detail below with reference to FIGS. 6 and 9.

A photoreceiver 11 functions as an optical receiver unit that converts an optical signal output from the control unit 8 into an electric signal. A low-pass filter 12 cuts off a harmonic component of the pulse-width modulated signal output from the photoreceiver 11 and outputs a smooth sine wave signal. Thereafter, a linear amplifier 13 functioning as a liner amplifier device linearly amplifies the sine wave signal output from the low-pass filter 12 and applies the sine wave signal to the vibration-type actuator.

Configuration of Vibration-Type Actuator

Figure 2:
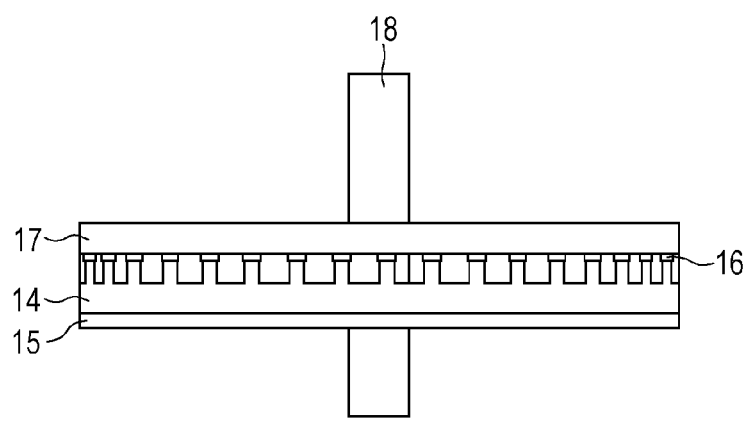
FIG. 2 is a schematic illustration of an exemplary configuration of a vibration-type actuator.

An exemplary configuration of the vibration-type actuator according to the present exemplary embodiment is described next. FIG. 2 is a schematic illustration of an exemplary configuration of the vibration-type actuator. According to the present exemplary embodiment, the vibration-type actuator includes a vibrating member and a driven member.

The vibrating member includes an elastic body 14 and a piezoelectric body 15 formed from a piezoelectric device (an electro-mechanical transducer). The elastic body 14 has a ring shape having a comb structure on one face. The piezoelectric body 15 is bonded to the other face of the elastic body 14. A friction member 16 is bonded at the top of a protrusion of the comb structure of the elastic body 14. A rotor 17, which is the driven member, has a disc-shaped structure. The rotor 17 is in pressure contact with the elastic body 14 via the friction member 16 by a pressure applying unit (not illustrated).

When an alternating-current voltage (a driving voltage) is applied to the piezoelectric body 15, vibration of the elastic body 14 of the vibration-type actuator is excited. This vibration rotates the rotor 17 relative to the elastic body 14 due to a frictional force generated between the rotor 17 and the friction member 16. A rotation shaft 18 is fixed to the rotor 17 at the center of the rotor 17 and rotates together with the rotor 17. According to the present exemplary embodiment, such a vibration-type actuator is disposed in each the two joints (indicated by circles in the robot arm 7 illustrated in FIG. 1) and the connection portion between the bed 5 and the base portion of the robot arm 7 so as to provide rotation about the two joints and rotation of the whole robot arm 7.

Figure 3:
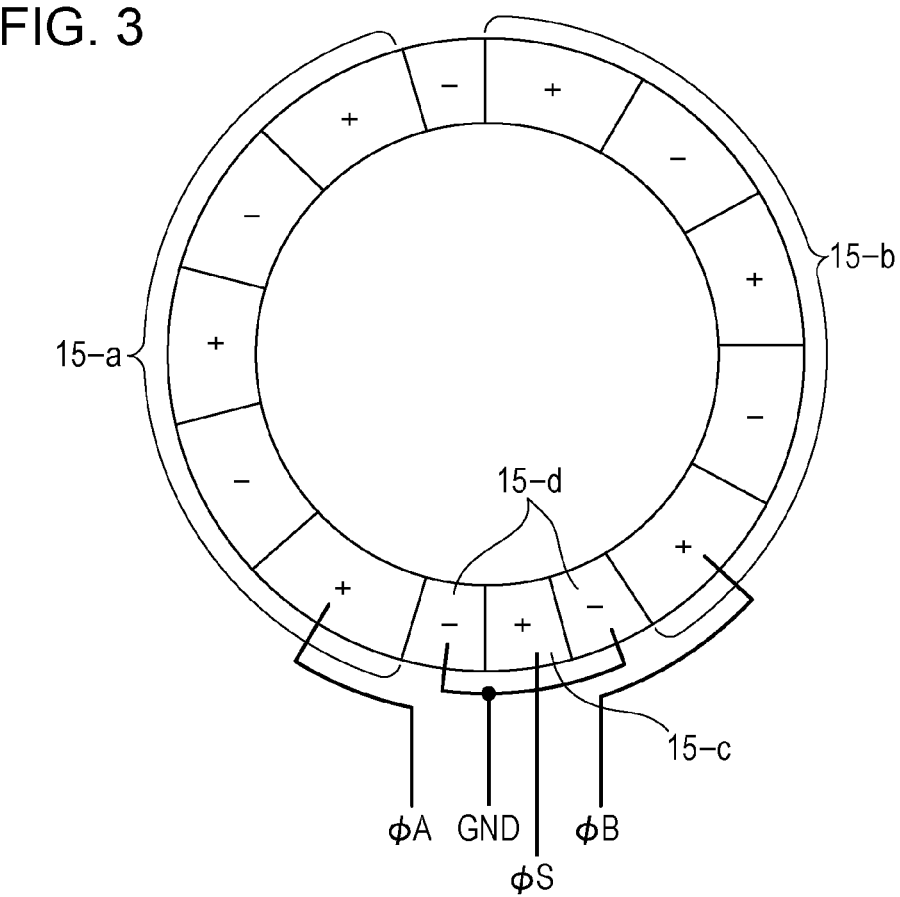
FIG. 3 is a plan view of a piezoelectric body.

FIG. 3 is a plan view of the piezoelectric body 15. The piezoelectric body 15 includes a piezoelectric material and a ring-shaped electrode formed on the piezoelectric material. The electrode is divided into a plurality of partitions. The plus or minus sign in FIG. 3 indicates the polarization direction of a portion of the piezoelectric material corresponding to each of the electrodes. In addition, the entire back face of the piezoelectric body 15 serves as a single electrode having electrical continuity. The electrodes fall into three groups: vibration electrodes 15-a and 15-b, a vibration detecting electrode 15-c, and ground connection electrodes 15-d. The three groups are electrically independent of one another. In each of the groups, the electrodes are connected using, for example, a conductive coating material (not illustrated). The ground connection electrodes 15-d are electrically connected to the elastic body 14 bonded to the back surfaces of the ground connection electrodes 15-*d* using a conductive coating material. Alternating-current voltages φA and φB having different phases are applied to the vibration electrodes 15-*a* and 15-*b*, respectively. Thus, a traveling vibration wave that propagates along the periphery of the ring of the elastic body 14 is generated.

Basic Structure of Drive Circuit of Vibration-Type Actuator

Referring back to FIG. 1, the drive circuit functioning as a driving apparatus that drives the vibration-type actuator according to the present exemplary embodiment is described in detail next. According to the present exemplary embodiment, the drive circuit of the vibration-type actuator includes the low-pass filter 12 and the linear amplifier 13. The linear amplifier 13 is an A-class or AB-class amplifier. The linear amplifier 13 outputs a waveform having low harmonic distortion.

As noted above, according to the present exemplary embodiment, the driving waveform signal output from the control unit 8 is a pulse signal obtained by performing pulse width modulation on a sine wave. The pulse-width modulated signal is converted into an optical signal in the control unit 8 and is transferred to the inside of the magnetic shield room 1 using the optical fiber 10 functioning as the optical waveguide unit.

The photoreceiver 11 converts the optical signal output from the control unit 8 into an electric signal (an alternating current voltage signal, which is a pulse signal obtained by performing pulse width modulation on a sine wave). The low-pass filter 12 cuts off a harmonic component of the pulse-width modulated signal output from the photoreceiver 11 and outputs a smooth sine wave signal. That is, by using the low-pass filter 12, at least a frequency component that is higher or equal to the modulation frequency of the pulse signal obtained by performing pulse width modulation on a sine wave is cut off. The above-described pulse signal has a waveform obtained by performing pulse width modulation (PWM) on a sine wave. However, another pulse modulation technique may be employed. Even from a waveform obtained by using pulse density modulation (PDM), such as ΔΣ modulation technique, or pulse amplitude modulation (PAM), an original sine wave can be obtained by using a filter that cuts off a high-frequency component.

Subsequently, a sine wave (an analog signal) obtained by cutting off a frequency component that is higher than or equal to the modulation frequency of the pulse-width modulated signal is input to the linear amplifier 13 functioning as the liner amplifier device as a signal based on the driving waveform output from the low-pass filter 12. The linear amplifier 13 linearly amplifies the input sine wave and applies the amplified drive voltage to the vibration-type actuator. Thus, a harmonic caused by the linear amplifier 13 is negligible. Note that since the above-described PDM is close to a frequency modulation technique, modulation frequency does not appear. In the above-described example, a sine wave obtained by cutting off a frequency component that is higher than or equal to the modulation frequency of the pulse-width modulated signal is used. Alternatively, a low-pass filter that cuts off a frequency that is higher than the frequency of the original sine wave may be employed. For example, in the case of PDM, by using a low-pass filter that cuts off a frequency that is higher than or equal to twice the frequency of the original sine wave, high-frequency waveform distortion can be cut off.

Unfortunately, the performance of a low-pass filter is limited. Accordingly, high-frequency waveform distortion caused by pulse modulation, such as pulse width modulation, cannot be completely eliminated. Note that the Larmor frequency is determined by the magnitude of the magnetic flux density of the magnetic field generated by the superconducting magnet 2 and the gradient magnetic field generation coil 3. Since the Larmor frequency varies with a variation of the magnetic flux density, the Larmor frequency is in a certain frequency range if the gradient magnetic field is provided.

According to the present exemplary embodiment, by selecting a modulation frequency so that a frequency that is an integral multiple of the modulation frequency of the above-described pulse width modulation is not included in the Larmor frequency range, noise coupling into an MR image can be reduced more. In particular, if the driving waveform is a pulse signal obtained by performing pulse width modulation or pulse amplitude modulation on a sine wave, it is desirable that a frequency that is an integer multiple of the modulation frequency of the pulse signal not be included in the Larmor frequency range. That is, if a signal based on the driving waveform is a sine wave including a harmonic, setting can be performed so that the harmonic is not included in the Larmor frequency range.

In addition, to reduce noise, it is effective to set the frequency of the drive voltage of the vibration-type actuator so that other harmonic components generated in pulse width modulation are not included in the Larmor frequency range. Examples of other harmonic components generated in pulse width modulation include a frequency component that is an integer multiple of the drive frequency, a frequency component that is the sum of a frequency component that is an integer multiple of the drive frequency and a frequency that is an integer multiple of the pulse width modulation frequency, and a frequency component that is the difference between a frequency component that is an integer multiple of the drive frequency and a frequency that is an integer multiple of the pulse width modulation frequency.

Furthermore, in the case in which the drive waveform is a signal obtained by D/A-converting a sine wave, it is also desirable that a frequency that is an integer multiple of the sampling frequency of D/A conversion not be included in the Larmor frequency range.

Figure 4:
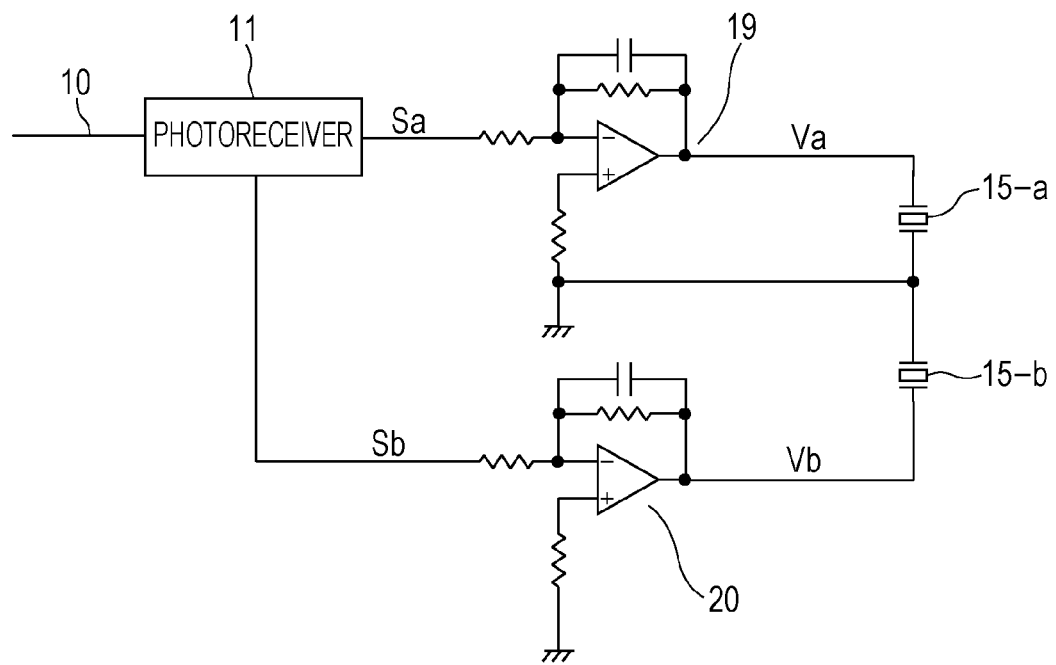
FIG. 4 is a schematic illustration of a modification of the present exemplary embodiment.

To control the speed of the vibration-type actuator, the drive frequency is controlled, in general. By presetting a frequency range of the drive waveform so that the harmonic generated by pulse width modulation is close to the Larmor frequency and controlling the frequency of the drive voltage outside the frequency range, noise contamination in the MR image can be reduced. Alternatively, if some level of noise contamination in a portion other than the portion of interest is allowed, the above-described Larmor frequency range may be decreased to the Larmor frequency range in the vicinity of the portion of interest. First Modification of First Exemplary Embodiment A first modification of the drive circuit according to the present exemplary embodiment is described next with reference to FIG. 4. While the first exemplary embodiment has been described with reference to the basic configuration in which the output of the photoreceiver 11 is input to the low-pass filter 12, which cuts off the modulation frequency of the PWM signal, the first modification provides the photoreceiver 11 having a filter property. FIG. 4 illustrates a drive circuit according to the modification of the present exemplary embodiment. According to the present modification, the photoreceiver 11 receives, via an optical fiber, pulse signals Pa and Pb obtained by performing pulse width modulation on a sine wave. The photoreceiver 11 according to the present modification has a low-pass filter function. The photoreceiver 11 cuts off the modulation frequency of the PWM signals and outputs sine wave signals Sa and Sb having different phases.

In addition, according to the present modification, the drive circuit includes inverting linear amplifiers 19 and 20 that are band-limited using a capacitor. If the filter property of the photoreceiver 11 is not sufficient, the sine wave signals Sa and Sb (the signals based on a drive waveform) may still have the above-described modulation frequency component signal. Therefore, according to the present modification, the modulation frequency component is further attenuated using the linear amplifiers 19 and 20 each including a capacitor, and alternating-current voltages Va and Vb serving as the drive voltages are applied to the piezoelectric bodies 15-$a$ and 15-$b$, respectively. Note that if, unlike the above-described example, the photoreceiver 11 has a filter property that provides sufficiently limited frequency band, the linear amplifiers 19 and 20 need not be band-limited using a capacitor.

Figure 5:
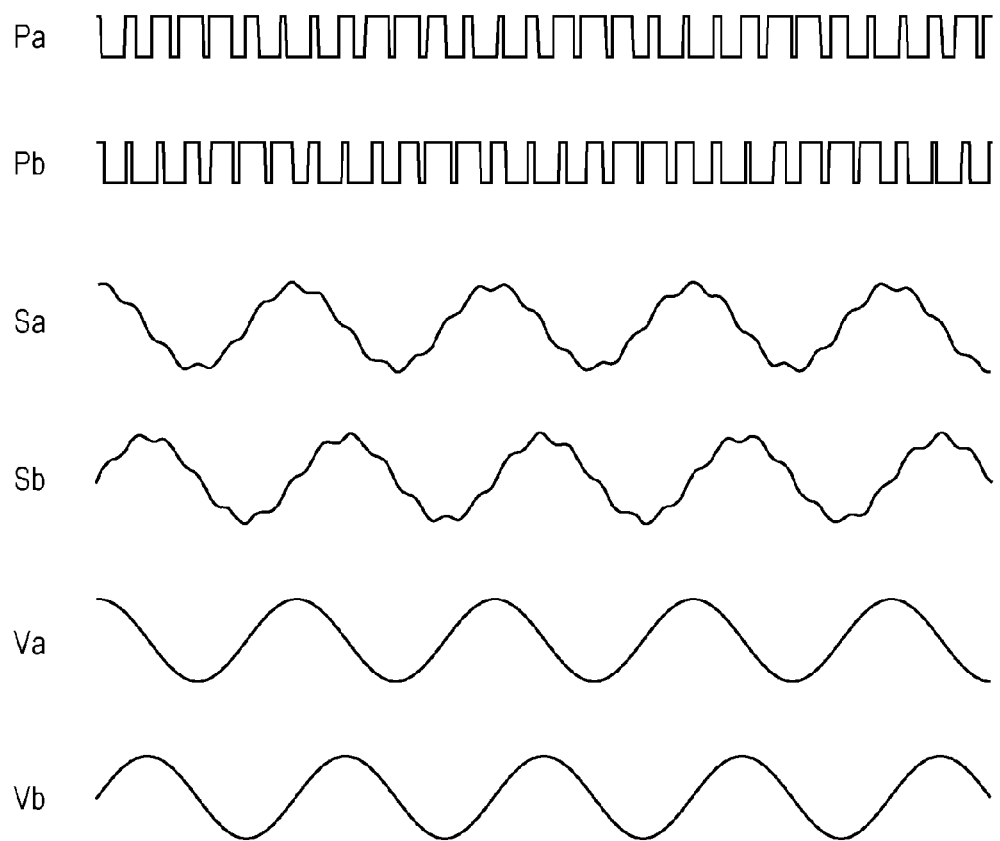
FIG. 5 is a schematic illustration of operating waveforms of units according to the modification of the first exemplary embodiment.

FIG. 5 is a schematic illustration of distortion of operating waveforms occurring in the units illustrated in FIG. 4. The signals Sa and Sb still contain modulation frequency component signals of the pulse signals Pa and Pb obtained by performing the pulse width modulation on a sine wave, respectively. However, the alternating-current voltages Va and Vb serving as the drive voltages applied to the piezoelectric bodies 15-$a$ and 15-$b$ negligibly contain the modulation frequency component signals. Note that even in such a case, a slight electromagnetic wave may have an impact on the MR image. Accordingly, it is desirable that a frequency that is an integer multiple of the pulse width modulation frequency not be included in the Larmor frequency range.

Second Modification of First Exemplary Embodiment

Figure 6:
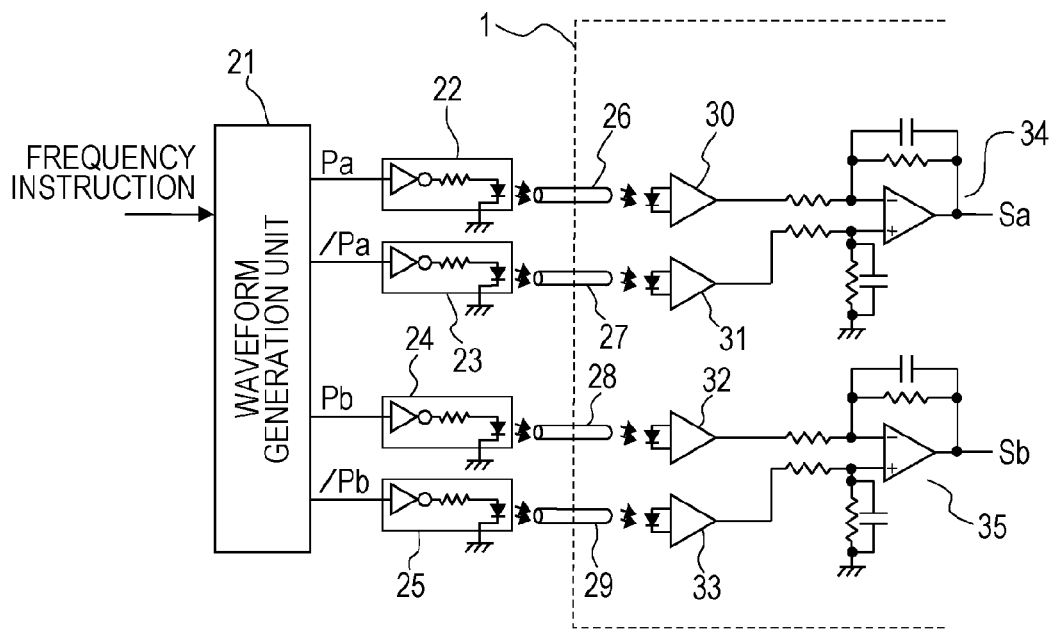
FIG. 6 is a schematic illustration of an example of an optical waveguide unit that connects the inside to the outside of a magnetic shield room.

A drive circuit according to a second modification of the present exemplary embodiment is described next with reference to FIG. 6. FIG. 6 illustrates signal connections between the inside and outside of the magnetic shield room 1 using optical fibers (the optical waveguide units). A waveform generation unit 21 generates pulse signals Pa, /Pa, Pb, and /Pb having different phases and obtained by performing pulse width modulation on sine wave signals in response to a frequency instruction received from an instructing unit (not illustrated). The waveform generation unit 21, the instructing unit, and transmitters 22 to 25 are disposed in the control unit 8 illustrated in FIG. 1.

As described above, the pulse signals Pa, /Pa, Pb, and /Pb are obtained by performing pulse width modulation on sine wave signals. The phases of the sine wave signals of the pulse signals Pa and Pb are opposite to those of the pulse signals /Pa and /Pb, respectively. In addition, the phase of the sine wave signal of the pulse signal Pa is shifted from that of the pulse signal Pb by 90°. Transmitters 22, 23, 24, and 25 each serving as the optical transmitter unit convert pulse-width modulated signals to optical signals. The optical signals output from the transmitters 22, 23, 24, and 25 are transferred to the inside of the magnetic shield room 1 via optical fibers 26, 27, 28, and 29 each functioning as the optical waveguide unit, respectively. Receivers 30, 31, 32, and 33 function as optical receiver units that convert the optical signals output from the optical fibers 26, 27, 28, and 29 into electric signals (alternating-current voltage signals), respectively. The electric signals are output in the form of pulse signals of a TTL level.

A differential amplifier 34 amplifies the difference between the output signals output from the receivers 30 and 31, and a differential amplifier 35 amplifies the difference between the output signals output from the receivers 32 and 33. In addition, each of the differential amplifiers 34 and 35 has a filter property for cutting off a frequency that is higher than or equal to a harmonic component related to the modulation frequency of the input pulse width modulated signal. That is, according to the present modification, the differential amplifier 34 functions as a low-pass filter. Furthermore, according to the present modification, the receivers 30 and 31 and the differential amplifier 34 form a photoreceiver.

Figure 7:
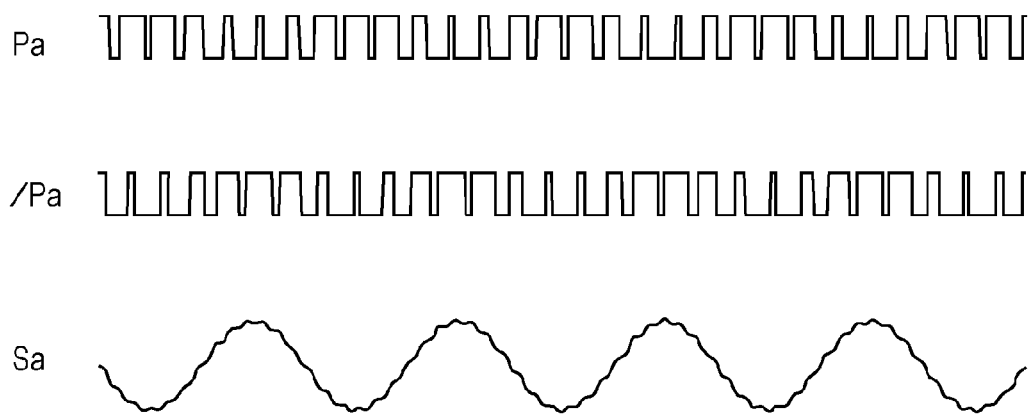
FIG. 7 is a schematic illustration of operating waveforms of the units illustrated in FIG. 6.

FIG. 7 is a schematic illustration of operating waveforms of the units illustrated in FIG. 6. As can be seen from FIG. 7, in the configuration including a differential amplifier according to the present modification, a modulation frequency component of pulse width modulation is canceled out. Accordingly, even a relatively mild filter property can reduce harmonic distortion. However, FIG. 7 indicates that although a modulation frequency component of pulse width modulation is canceled out, a frequency component in the vicinity of a frequency that is twice the modulation frequency still remains. The frequency component in the vicinity of a frequency that is twice the modulation frequency can be reduced by, for example, connecting the linear amplifiers 19 and 20 having a capacitor illustrated in the first modification to the output destination of the differential amplifier.

Figure 8:
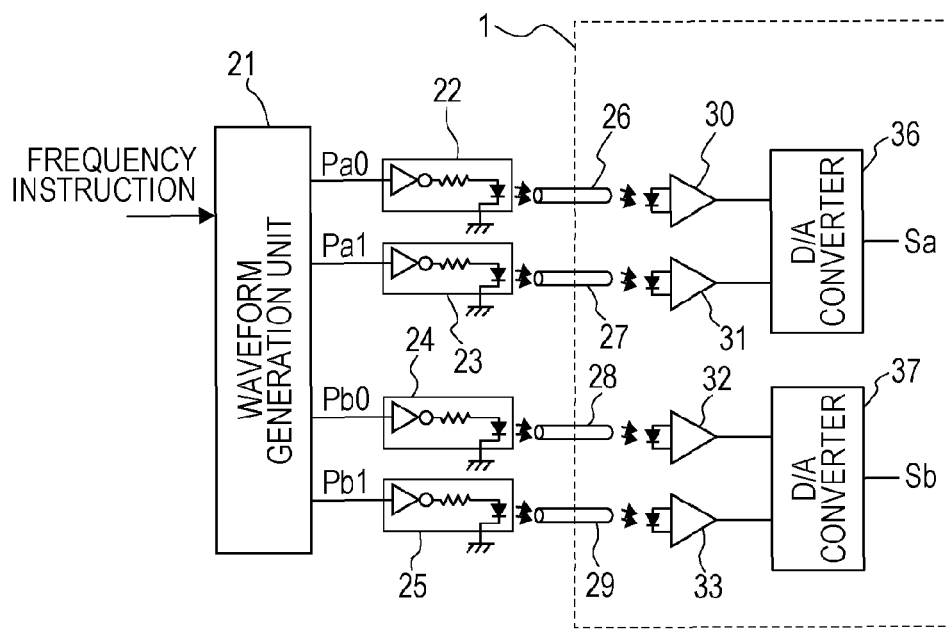
FIG. 8 illustrates an example in which a D/A converter is used instead of a differential amplifier illustrated in FIG. 6.

Furthermore, according to the present exemplary embodiment, as illustrated in FIG. 8, a D/A converter may be employed instead of the differential amplifier illustrated in FIG. 7. Each of D/A converters 36 and 37 is a 2-bit D/A converter. Instead of the pulse signals obtained by performing pulse width modulation on four sine waves having different phases, the waveform generation unit 21 outputs two pairs of sine wave signals having different phases, each pair representing a 2-bit signal. The waveforms of the sine wave signals are formed as parallel signals Pa0 and Pa1 representing 2 bits and parallel signals Pb0 and Pb1 representing 2 bits. The sine wave signals Pa0 and Pa1 are transmitted to the D/A converter 36 via the optical fibers 26 and 27, respectively. The sine wave signals Pb0 and Pb1 are transmitted to the D/A converter 37 via the optical fibers 28 and 29, respectively. The design is such that if the inputs to the D/A converters 36 and 37 change, the D/A converters 36 and 37 immediately change the values of their analog output signals. In addition, each of the D/A converters 36 and 37 includes a low-pass filter that cuts off a frequency component that is higher than or equal to the frequency of the sine wave signal. Thus, each of the D/A converters 36 and 37 outputs a sine wave having a smooth waveform. Furthermore, the D/A converters 36 and 37 illustrated in FIG. 8 operate in response to input of parallel signals. However, by using an existing D/A converter that operates in response to input of a serial signal, a multi-bit signal may be transmitted.

Figure 9:
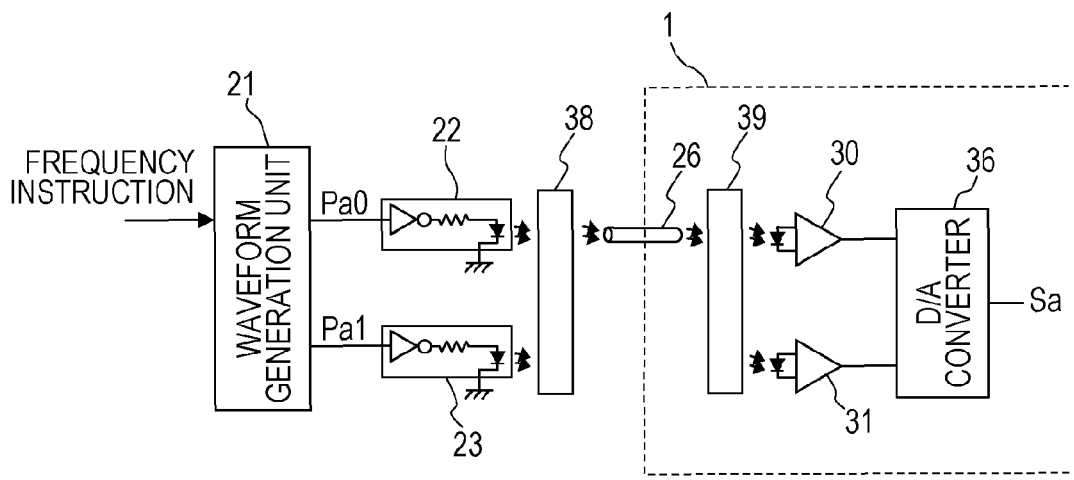
FIG. 9 is a schematic illustration of an example of the optical waveguide unit using optical wavelength division multiplexing transmission.

The optical waveguide unit using optical wavelength division multiplexing transmission is described next. FIG. 9 is a schematic illustration of an example of the optical waveguide unit using optical wavelength division multiplexing transmission. Since the configurations other than the configuration related to optical transport are the same as those of FIG. 8, description of the configurations is not repeated.

When a large number of signal lines that extend between the inside and outside of the magnetic shield room 1 are required, the number of optical fibers increases. Therefore, according to the present exemplary embodiment, each of signals is converted into the wavelength of a light beam. Thereafter, the light beams having different wavelengths are combined, and a combined light beam is transmitted. In this manner, a plurality of signals can be transmitted by a single optical fiber.

The transmitters 22 and 23 each functioning as the optical transmitter unit receive driving waveform signals and converts the driving waveform signals into optical signals having different wavelengths. An optical combining unit 38 combines the light beams that have different wavelengths and that are output from the transmitters 22 and 23. Thereafter, the optical combining unit 38 outputs the combined light beam to the optical fiber 26. An optical distribution unit 39 separates the light beam (a combined light beam signal) output from the optical fiber 26 by wavelength and outputs the separate light beams to the receivers 30 and 31. Each of the receivers 30 and 31 converts the input optical signal into an electric signal.

While the present exemplary embodiment has been described with reference to the pulse signal converted into an optical signal and, thereafter, transmitted, the output of an existing sine wave oscillator, such as Wien bridge, may be converted into an optical signal and be transmitted. In this manner, the need for a digital signal can be completely eliminated. Thus, it is advantageous for applications that are sensitive to noise. Note that at that time, to correct the difference in photoreceptive sensitivity between the receivers 30 and 31, it is desirable that the amplitudes be independently adjusted. In addition, while the present exemplary embodiment has been described with reference to transmission of a signal from the outside to the inside of the magnetic shield room 1 using an optical fiber serving as the optical waveguide unit, the optical signal may be directly transmitted using optical space transmission through a window (not illustrated) of the magnetic shield room 1 that transmits a light beam.

As described above, according to the present exemplary embodiment, by transmitting, from the waveform generating unit, a driving waveform signal used for driving the vibration-type actuator in the form of an optical signal, electromagnetic noise transferred from the waveform generating unit can be reduced. In addition, a time delay and degradation of a driving waveform are small. Thus, even when a remote vibration-type actuator is controlled, the parameters of the driving waveform can be set in real time.

In addition, by disposing, for example, the waveform generating unit that requires a high-frequency clock signal outside the magnetic shield room, transfer of magnetic noise caused by the clock signal can be blocked. Accordingly, even when the vibration-type actuator is driven together with the measuring unit of the MRI apparatus, noise contamination in an MR image can be reduced. Thus, a medical doctor can easily provide medical treatments while viewing MR images in real time. Furthermore, by transmitting the drive voltage from the outside to inside of the magnetic shield room in the form of an optical signal, the length of an electric cable that transmits the drive voltage to the vibration-type actuator can be reduced and, therefore, the circuit efficiency can be improved.

Furthermore, while the present exemplary embodiment has been described with reference to the vibration-type actuator driven during the operation performed by the MRI apparatus, any apparatus disposed in the magnetic shield room for measuring an electromagnetic wave or magnetism can have the same advantage. For example, a magnetoencephalograph (MEG) measures a low magnetic field generated by an electric current flowing for signal transfer in the nerve of the brain of an examinee. A MEG is often used to supplement fMRI measurement when the above-described response to a stimulus applied to the examinee is examined. Accordingly, like the MRI apparatus, external electromagnetic noise included in the magnetic field needs to be blocked as much as possible. According to the present exemplary embodiment, measurement with less noise is available.

Figure 10:
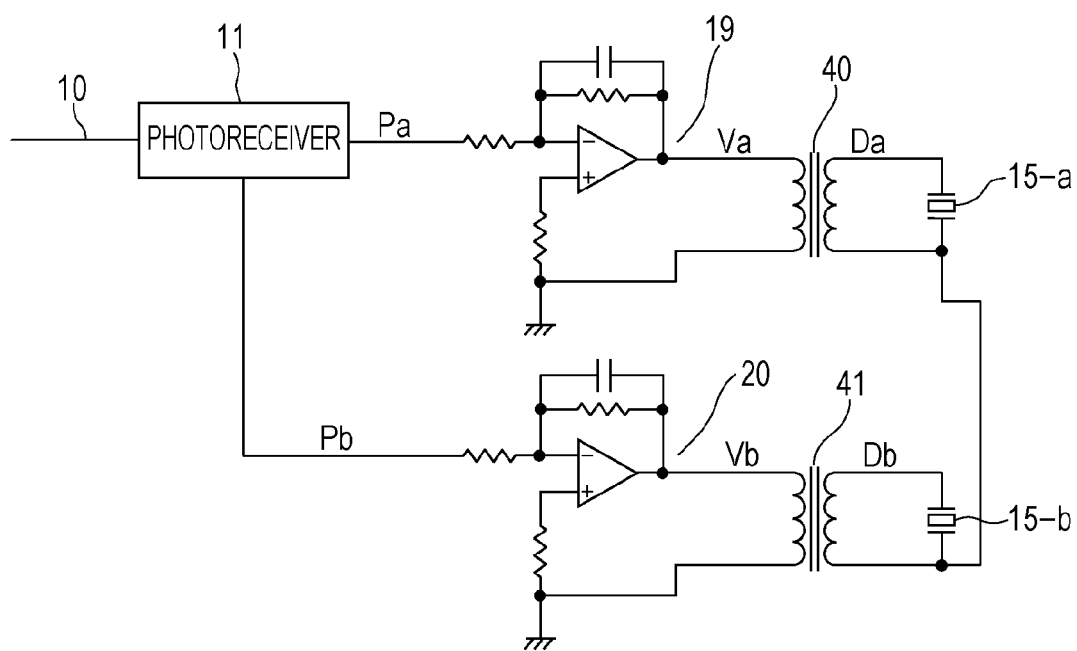
FIG. 10 is a schematic illustration of a drive circuit of a vibration-type actuator according to a second exemplary embodiment.

Still furthermore, while the present exemplary embodiment has been described with reference to the system for measuring brain blood current of an examinee by stimulating the examinee as an example of a medical care system, the present exemplary embodiment is also applicable to a robot that performs medical treatments or biopsy and a transfusion system using an MRI. By using the technology according to the present exemplary embodiment, an excellent image can be obtained even when the vibration-type actuator operates during MR image measurement in such systems. Second Exemplary Embodiment A second exemplary embodiment of the present disclosure is described next. FIG. 10 illustrates a drive circuit of a vibration-type actuator according to the second exemplary embodiment. According to the present exemplary embodiment, a transformer is connected between the linear amplifier 19 and the piezoelectric body 15-*a* of the vibration-type actuator, and another transformer is connected between the linear amplifier 20 and the piezoelectric body 15-*b* of the vibration-type actuator. In addition, the ground is electrically insulated. That is, a linear amplifier is connected to the primary side of the transformer, and the vibration-type actuator is connected to the secondary side of the transformer. The drive voltage output from the linear amplifier is applied to the vibration-type actuator via the transformer. Accordingly, some of common mode noise coupling from a power supply lines of the linear amplifiers 19 and 20 into the vibration-type actuator can be blocked.

The configuration of the drive circuit illustrated in FIG. 10 is obtained by adding transformers 40 and 41 to the configuration illustrated in FIG. 4. Note that the operation performed by the photoreceiver 11 differs from that in FIG. 4. Since the photoreceiver 11 illustrated in FIG. 4 has a low-pass filter property, the output signal has a substantially sine wave waveform on which the signal of modulation frequency component of pulse width modulation is overlaid. In contrast, according to the present exemplary embodiment, the photoreceiver 11 outputs the pulse signals Pa and Pb obtained by performing the pulse width modulation on a sine wave.

Figure 11:
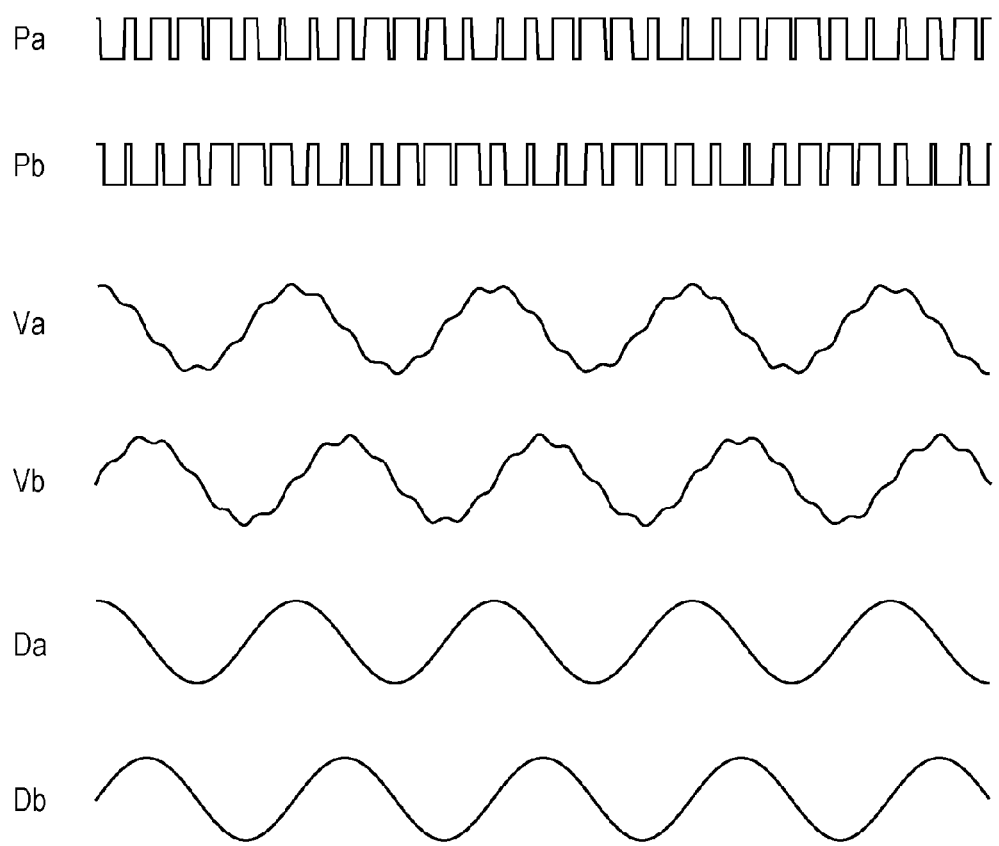
FIG. 11 is a schematic illustration of the operating waveforms of the units illustrated in FIG. 10.

FIG. 11 is a schematic illustration of the operating waveforms of the units illustrated in FIG. 10. The pulse signals Pa and Pb are obtained by performing the pulse width modulation on a sine wave. The magnitude of each of the high-level pulse signals Pa and Pb is the same as the magnitude of each of the low-level pulse signals Pa and Pb, but the signs thereof differ from each other.

The linear amplifiers 19 and 20 each including a capacitor have a low-pass filter property. Thus, each of the output alternating-current voltages Va and Vb is in the form of a sine wave having a signal of the modulation frequency of pulse width modulation overlaid thereon. In addition, each of signals Da and Db on the secondary sides of the transformers 40 and 41 (on the sides of the piezoelectric bodies 15-*a* and 15-*b* of the piezoelectric bodies) is in the form of a smooth sine wave with a pulse width modulation frequency component removed. This is because the pulse width modulation frequency component is cut off by the low-pass filter property that is determined by the leakage inductances of the transformers 40 and 41 and the damped capacitances of the piezoelectric bodies 15-*a* and 15-*b*. By setting the leakage inductance of the transformer in this manner, the filter structure can be simplified. In addition, in the above-described example, the filter is disposed in the transformer and upstream of the transformer. However, the filter may be disposed downstream of the transformer.

Figure 12:
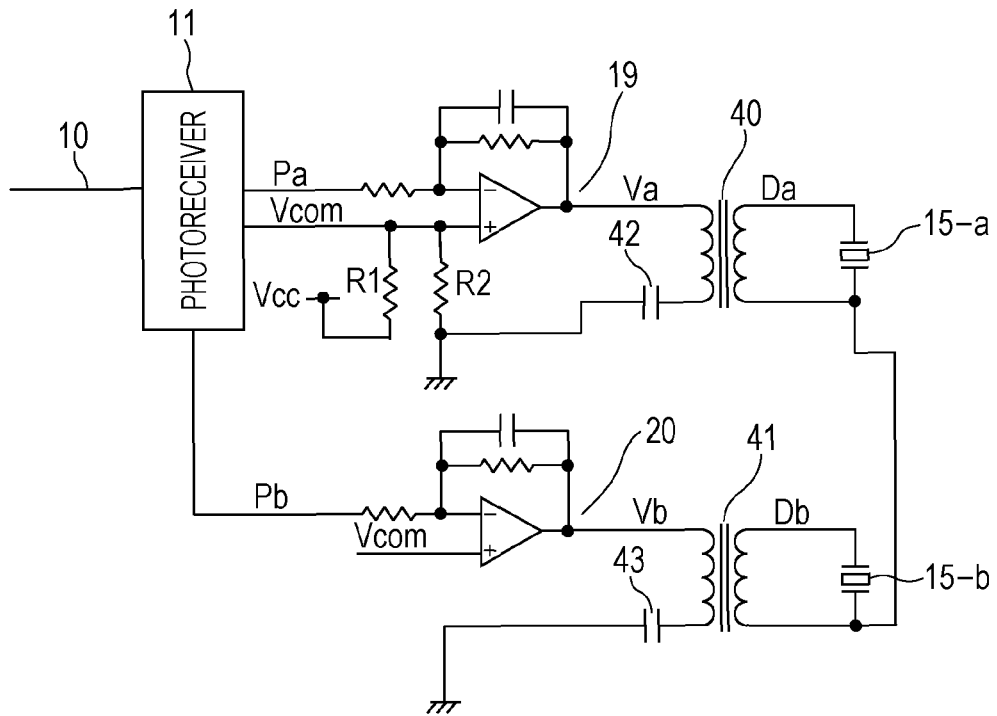
FIG. 12 is a schematic illustration of an example of the drive circuit according to a first modification of the second exemplary embodiment.

Drive Circuit According to First Modification of Second Exemplary Embodiment A drive circuit according to a first modification of the present exemplary embodiment is described next. FIG. 12 illustrates a drive circuit of the vibration-type actuator according to the modification of the second exemplary embodiment. In general, a linear amplifier outputs a certain offset voltage even when the input voltage is set to 0 V. Accordingly, if, as illustrated in FIG. 11, a linear amplifier is connected to the primary side of the transformer and is allowed to operate without current limitation, a large current flows as the output and, therefore, the transformer and the linear amplifier may be damaged. In addition, even when the offset voltage is adjusted to substantially 0 V, a power source supplied to the linear amplifier requires plus and minus polarity power sources. Accordingly, the scale of the apparatus may increase. To solve such a problem, a current limiting circuit may be provided in the linear amplifier, or a resistor may be connected in series to the primary side of the transformer so that a direct current is limited. However, this technique may increase electric power consumed when the vibration-type actuator is stopped. Thus, according to the present modification, a circuit configuration capable of limiting the electrical current and reducing power consumption is described next.

In a drive circuit illustrated in FIG. 12, direct currents flowing in the primary sides of the transformers 40 and 41 are blocked by capacitors 42 and 43 connected in series to the primary sides of the transformers 40 and 41, respectively. Thus, the linear amplifier can operate using a single power source (a voltage Vcc). An exemplary operation performed by the drive circuit illustrated in FIG. 12 is described below. The voltage Vcc is a power supply voltage for the linear amplifiers 19 and 20. In addition, the voltage Vcc is divided by resistors R1 and R2, and a common voltage Vcom is generated. The common voltage Vcom is input to the positive polarity inputs of the linear amplifiers 19 and 20 and the common voltage input of the photoreceiver 11.

Figure 13:
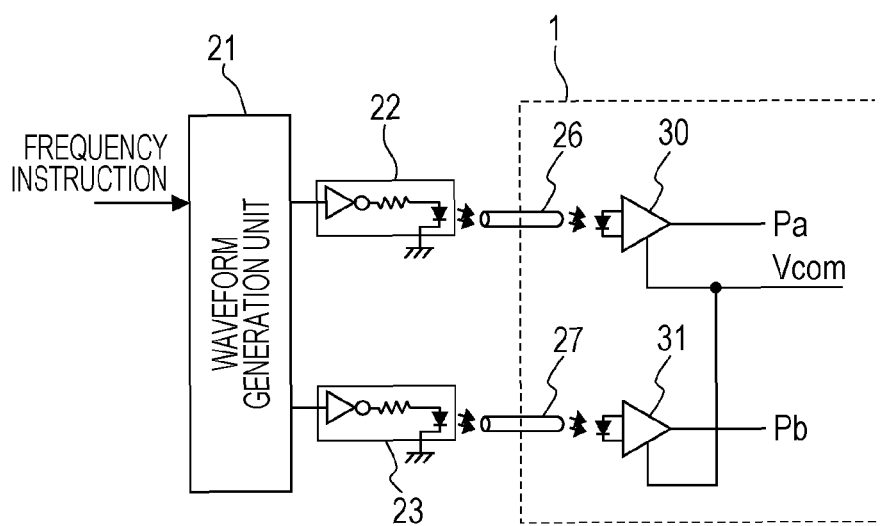
FIG. 13 is a schematic illustration of an example of the circuit configuration around a photoreceiver.

FIG. 13 illustrates an example of the circuit configuration around the photoreceiver 11. As illustrated in FIG. 13, the photoreceiver 11 illustrated in FIG. 12 is formed from two receivers, that is, the receivers 30 and 31. The optical fiber 10 is formed from two optical fibers, that is, optical fibers 26 and 27. An input signal output from the waveform generating unit is input via the optical fibers 26 and 27. Accordingly, outside the magnetic shield room 1, even a pulse signal based on the ground is received, the pulse signals Pa and Pb based on the common voltage Vcom can be generated.

Figure 14:
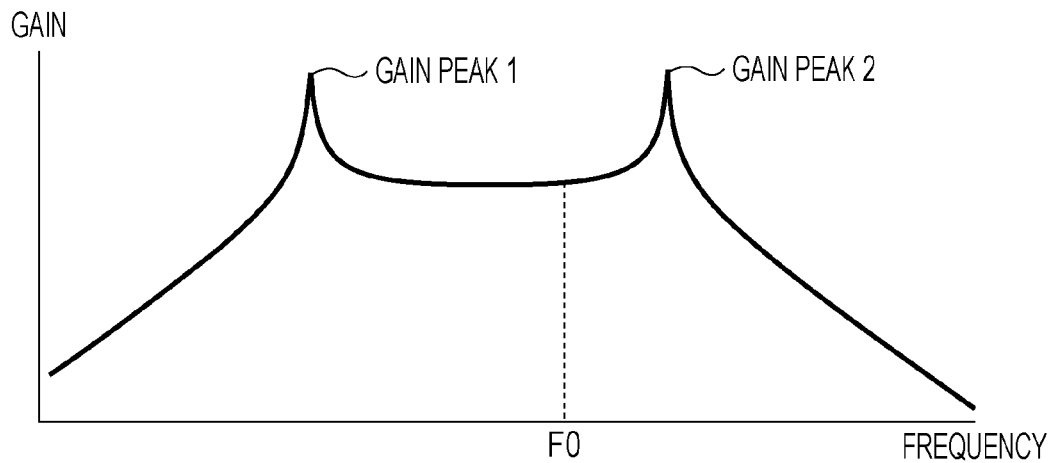
FIG. 14 illustrates the frequency characteristic of the gain in the circuit illustrated in FIG. 12.

FIG. 14 illustrates the gain-frequency characteristic from the input voltage Va to an output signal Da of the transformer 40 illustrated in FIG. 12. Since the capacitors 42 and 43 are disposed in order to block a direct current, a gain peak 1 caused by resonance between the primary side inductance of the transformers 40 and 41 and the capacitors 42 and 43 appears in the gain characteristic. In addition, a gain peak 2 caused by resonance between the leakage inductance of the transformers 40 and 41 and the damped capacitance of the piezoelectric bodies 15-$a$ and 15-$b$ appears in the gain characteristic. "F0" denotes the fundamental frequency of the sine wave applied to the piezoelectric bodies 15-$a$ and 15-$b$. This characteristic indicates that the circuit characteristic becomes oscillatory when the load imposed on the vibration-type actuator abruptly varies or the drive voltage varies. In such a case, noise may be generated.

To solve such a problem, as a first solution, a waveform is generated using a pulse width modulated waveform generation unit (not illustrated) so that abrupt voltage application is prevented and the amplitude of the voltage applied to the vibration-type actuator gradually varies (even when the vibration-type actuator is started or stopped).

As a second solution, the circuit design is performed so that the peak of the gain characteristic illustrated in FIG. 14 is sufficiently low. By applying the second solution, the interference caused by abrupt load variation that is difficult to avoid by only applying the first solution can be avoided. The second solution is described below with reference to FIG. 15.

Figure 15:
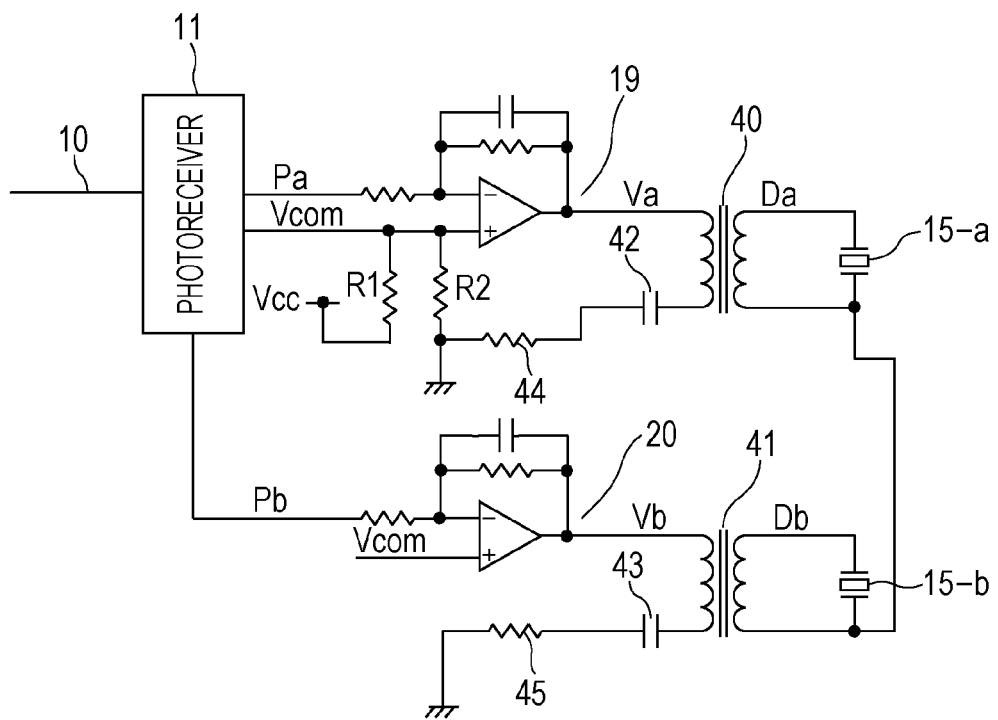
FIG. 15 is a schematic illustration of the drive circuit according to a second modification of the second exemplary embodiment.
Figure 16:
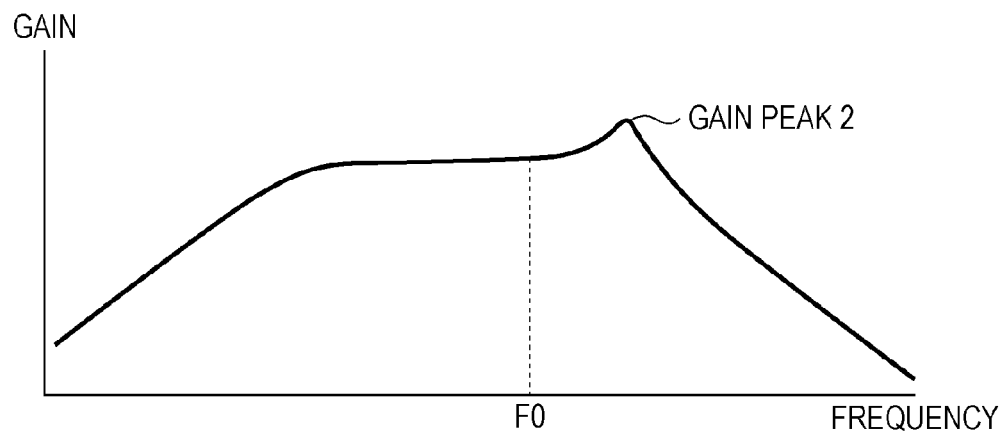
FIG. 16 illustrates the frequency characteristic of the gain in the circuit illustrated in FIG. 15.

Drive Circuit According to Second Modification of Second Exemplary Embodiment FIG. 15 illustrates a drive circuit according to a second modification of the present exemplary embodiment. According to the modification, resistors 44 and 45 are connected in series to the primary sides of the transformers 40 and 41 illustrated in FIG. 12. FIG. 16 illustrates the gain-frequency characteristic from the input voltage Va to an output signal Da of the transformer 41 in the circuit illustrated in FIG. 15. Since the resistors are connected in series to the primary sides of the transformers 40 and 41, the gain peak 1 and gain peak 2 are suppressed and, thus, the gain characteristic changes as in FIG. 16. As can be seen from FIG. 16, the gain peak 1 disappears. In addition, the gain peak 2 is suppressed. While the modification has been described with reference to a resistor in FIG. 15, any resistive element, such as a posistor, may be employed instead of the resistor.

Figure 17:
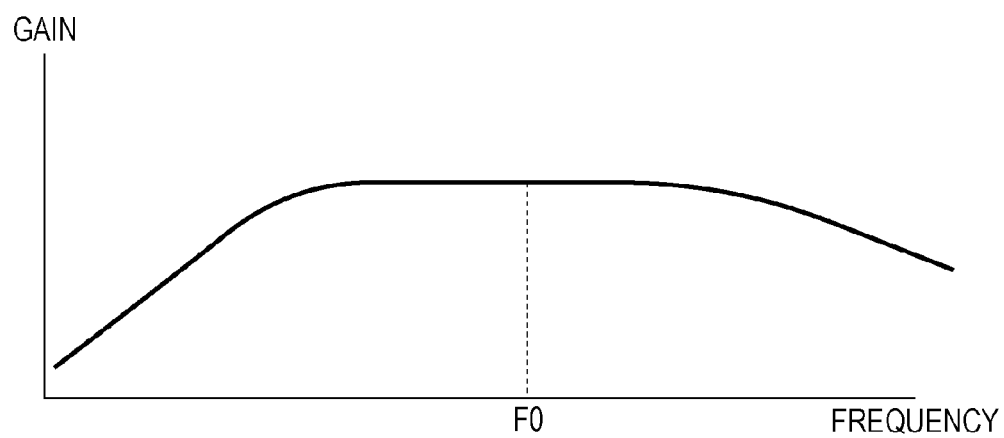
FIG. 17 illustrates the frequency characteristic of the gain when a toroidal core is used as the transformer.

Note that the reason for appearance of the gain peak 2 in FIG. 16 is that the attenuation caused by the resistors is insufficient. However, if the attenuation caused by the resistors is significantly increased, the efficiency decreases. Accordingly, to solve such a problem, the leakage inductance of the transformer can be decreased. FIG. 17 illustrates the gain characteristic when a toroidal core is used as the transformer to reduce the leakage inductance. As can be seen from FIG. 17, since the leakage inductance is reduced, the gain peak 2 disappears.

As described above, like the first exemplary embodiment, according to the present exemplary embodiment, by outputting, from the linear amplifier, the drive voltage to be applied to the vibration-type actuator, harmonic components included in the drive voltage can be reduced. Thus, harmonic component noise can be reduced. In addition, according to the present exemplary embodiment, the noise coupling from the power supply can be blocked by using a transformer. Furthermore, the gain peak characteristic that causes the occurrence of noise can be suppressed. In this manner, a robot arm used for, for example, medical care in cooperation with the MRI apparatus can be stably driven. In addition, the efficiency of a linear amplifier is lower than that of a switching amplifier, such as a D-class amplifier. Accordingly, by setting the resonance frequency determined by the secondary side inductance of the transformers 40 and 41 and the damped capacitance of the piezoelectric bodies 15-$a$ and 15-$b$ to a value substantially the same as the resonance frequency of the vibration-type actuator, the efficiency of each of the linear amplifiers 19 and 20 can be increased. For example, when the damped capacitance of the piezoelectric body is 7.8 nF and if the secondary side inductance is set to 3.4 mH, the resonance frequency is about 30.9 kHz. By setting this frequency to a value close to the drive frequency or the resonance frequency, power consumption of the linear amplifier at a frequency close to the resonance frequency can be reduced.

Furthermore, if the driving apparatus of the vibration-type actuator according to the present exemplary embodiment is applied to an apparatus disposed inside the magnetic shield room in addition to the MRI apparatus, the same advantage can be provided.

Third Exemplary Embodiment

Figure 18:
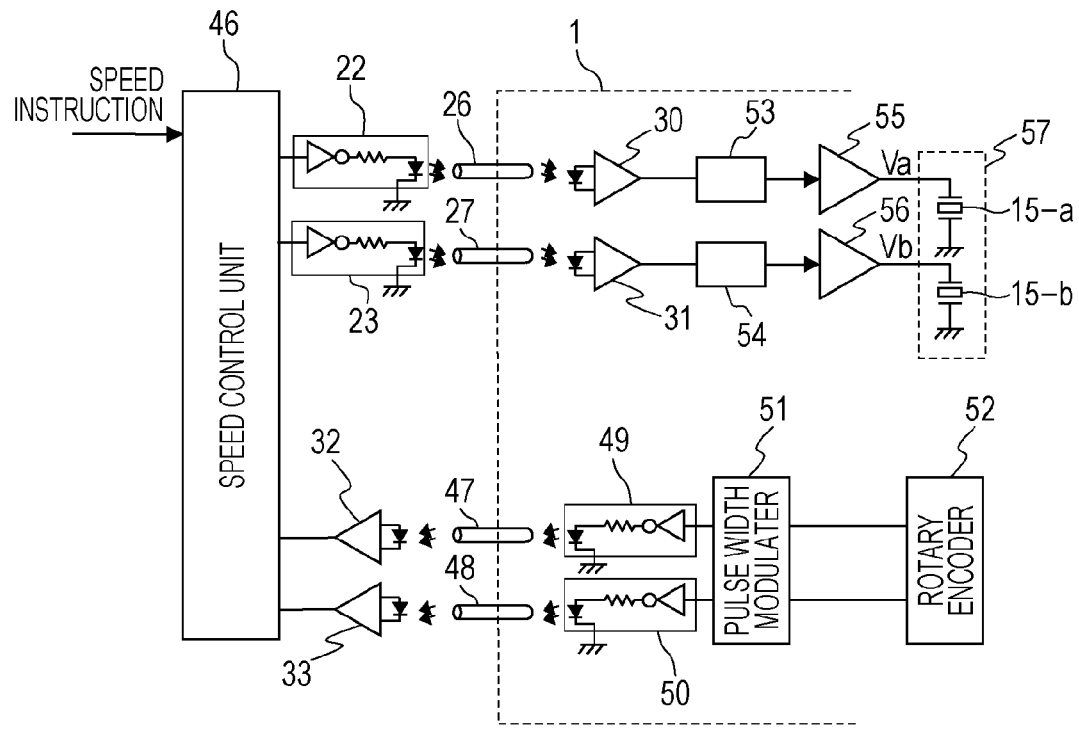
FIG. 18 is a schematic illustration of a drive circuit of a vibration-type actuator according to a third exemplary embodiment.

A third exemplary embodiment of the present disclosure is described next. FIG. 18 illustrates a measuring system according to the third exemplary embodiment of the present disclosure. According to the present exemplary embodiment, the inside and the outside of the magnetic shield room 1 are connected to each other via an optical fiber. The driving waveform signal of a vibration-type actuator is transmitted using a first optical signal, and an encoder signal (a detection signal) used for detecting the rotational position is transmitted using a second optical signal.

The driving waveform signal is converted into the first optical signals by the transmitters 22 and 23 each functioning as the first optical transmitter unit. The first optical signals output from the optical fibers 26 and 27 are converted into electric signals (first alternating current voltage signals) by receivers 30 and 31 each functioning as a first optical receiver unit, respectively. The first alternating current voltage signal is a pulse signal obtained by performing pulse width modulation on a sine wave signal.

A pulse signal obtained by performing pulse width modulation on a sine wave signal is input to each of low-pass filters 53 and 54. The harmonic components of the signal generated through pulse width modulation are cut off by the low-pass filters 53 and 54. Thereafter, the signals are input to linear amplifiers 55 and 56. The alternating-current voltages Va and Vb output from the linear amplifiers 55 and 56 are applied to the piezoelectric bodies 15-a and 15-b of the vibration-type actuator 57, respectively.

The frequencies, phases, and voltage amplitudes of the alternating-current voltages Va and Vb can be independently controlled in accordance with the pulse signal generated by a speed control unit 46. Accordingly, for example, by periodically changing the voltage amplitude and the phase in a predetermined pattern, traveling vibration waves that travel in different directions can be simultaneously generated in the ring-shaped elastic body of a vibration-type actuator 57. Thus, the vibration-type actuator 57 can be driven at a very low speed. Alternatively, a variety of other control techniques can be employed. For example, by changing the amplitude balance or the phase difference between the alternating-current voltages Va and Vb and, thus, changing a balance between a traveling wave and a standing wave, the force can be controlled. In this manner, the vibration-type actuator 57 can be smoothly driven across the range from low to high speed (even when the rotation direction is changed to the reverse rotation). Thus, the manipulator that requires highly accurate force control can be driven.

To detect the speed representing one of the drive states of the vibration-type actuator 57, a rotary encoder 52 outputs two-phase analog sine wave signal. The analog sine wave signal output from the rotary encoder 52 is pulse width modulated by a pulse width modulator 51. According to the present exemplary embodiment, the rotary encoder 52 and the pulse width modulator 51 form a detecting unit. Transmitters 49 and 50 function as a second optical transmitter unit that converts a pulse signal output from the pulse width modulator 51 (a detection signal) into a second optical signal.

The second optical signal is transmitted from the inside of the magnetic shield room 1 to the receivers 32 and 33 disposed outside the magnetic shield room 1 via optical fibers 47 and 48 functioning as a second optical waveguide unit. The receivers 32 and 33 functioning as a second optical receiver unit receive an optical signal and converts the optical signal into an electric signal (a second alternating-current voltage signal).

The speed control unit 46 measures each of the pulse widths of the pulse-width modulated signal s (the second alternating-current voltage signals) output from the receivers 32 and 33 and detects the wavelength of the analog sine wave signal output from the rotary encoder 52. Thereafter, the speed control unit 46 obtains a moving amount for a predetermined period of time using the result of detection and computes the speed of the vibration-type actuator, which is the drive state of the vibration-type actuator. Subsequently, the speed control unit 46 compares the instructed speed received from an instructing unit (not illustrated) with the result of computation. Thus, the speed control unit 46 determines the frequencies, the phases, and the amplitudes of the alternating-current voltages Va and Vb used for driving the vibration-type actuator 57 in accordance with the result of comparison. Note that according to the present exemplary embodiment, in addition to the speed, the drive state of the vibration-type actuator includes the position (the rotational position) of the vibrating member relative to the driven member and the acceleration of the driven member.

The determined alternating-current voltages Va and Vb are immediately pulse width modulated and are transmitted to the drive circuit inside the magnetic shield room 1 via the transmitters 22 and 23. Thereafter, the vibration-type actuator 57 operates so that the rotational speed is the same as the instructed speed. That is, according to the present exemplary embodiment, the speed control unit 46 functions as a control unit that controls at least one of the frequency, the phase, and the amplitude of the driving waveform signal. In addition, the speed control unit 46 functions as the waveform generating unit that generates the driving waveform signal.

In addition, while the present exemplary embodiment has been described with reference to the analog sine wave signal output from the rotary encoder 52 and pulse width modulated by the pulse width modulator 51, another pulse modulation technique may be employed. For example, a variety of modulation techniques, such as ΔΣ modulation or pulse amplitude modulation, can be employed. Furthermore, while the present exemplary embodiment has been described with reference to the speed control unit 46 that measures the pulse width of the pulse signal (the second alternating-current voltage signal) and detects the waveform of the analog sine wave signal, the waveform may be detected using an A/D converting unit (not illustrated) and be converted into an analog waveform using a digital low-pass filter. Alternatively, by disposing an analog filter (not illustrated) upstream of an A/D converting unit (not illustrated), the analog waveform can be also detected.

Figure 19:
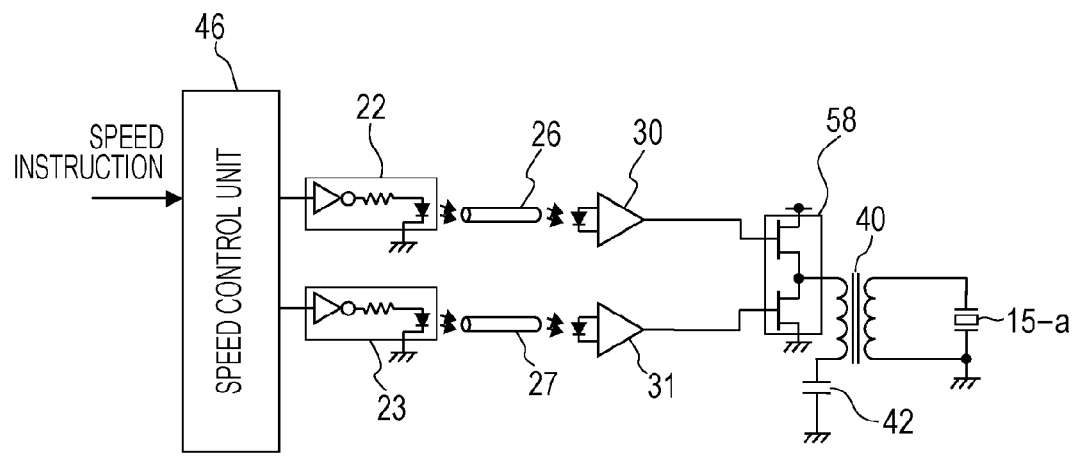
FIG. 19 is a schematic illustration of a drive circuit of the vibration-type actuator according to the third exemplary embodiment.

In addition, while the present exemplary embodiment has been described with reference to the vibration-type actuator 57 driven using a linear amplifier, the vibration-type actuator 57 can be driven using a D-class amplifier configuration including, for example, a bridge circuit. FIG. 19 illustrates an example in which an alternating-current voltage is applied to the piezoelectric body 15-a using a bridge circuit 58. A driving pulse is directly output from the speed control unit 46 to a field-effect transistor (FET) of the bridge circuit. Since the optical fibers 26 and 27 are provided for electrical insulation, a switching pulse can be supplied to a high-side FET of the bridge circuit 58 using a simplified circuit. Since this circuit is formed as a half-bridge circuit, the primary side of the transformer 40 has a configuration in which a direct current is cut by the capacitor 42.

Furthermore, while the present exemplary embodiment has been described with reference to four optical fibers, connection can be made using a single optical fiber if an optical wavelength division multiplexing technique is employed. Still furthermore, the number of the optical fibers can be reduced even when a plurality of vibration-type actuators are used. Yet still furthermore, the optical signal obtained by converting the driving waveform signal (i.e., the first optical signal) and the optical signal obtained by converting the detection signal (i.e., the second optical signal) can be transmitted using the same optical fiber.

Figure 20:
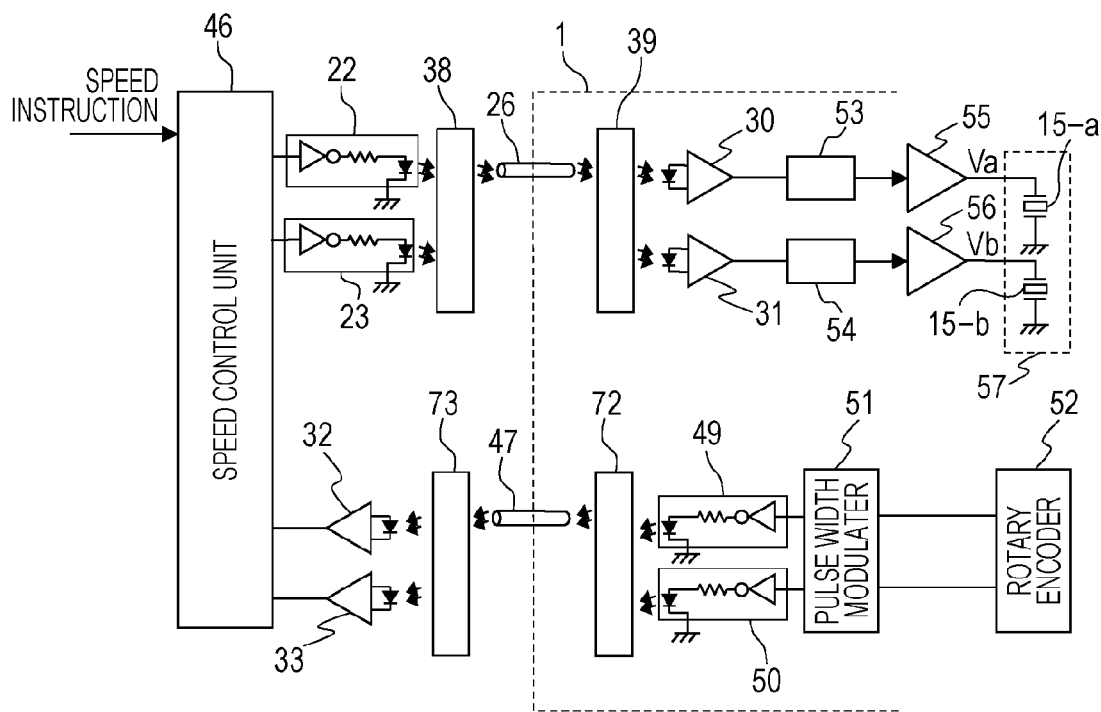
FIG. 20 is a schematic illustration of an example of an optical waveguide unit using optical wavelength division multiplexing.

A particular example is described below with reference to FIG. 20. FIG. 20 is a schematic illustration of an example of the optical waveguide unit using optical wavelength division multiplexing. In FIG. 20, transmitters 22 and 23 functioning as the first optical transmitter unit, a first optical combining unit 38, a first optical distribution unit 39, receivers 30 and 31 are similar to those according to the second modification (FIG. 9) of the first exemplary embodiment in which the operation performed for the first optical signal is described. Accordingly, descriptions are not repeated. As illustrated in FIG. 20, the transmitters 49 and 50 functioning as the second optical transmitter unit receives pulse signals (detection signals) output from the pulse width modulator 51 and converts the pulse signals into optical signals (the second optical signals) having different wavelengths. A second optical combining unit 72 combines the light beams output from the transmitters 49 and 50 and having different wavelengths and outputs a combined light beam signal to the optical fiber 47. A second light distribution unit 73 separates the light beam (the combined light beam signal) output from the optical fiber 47 by wavelength and outputs the separate light beams to the receivers 32 and 33. The other configurations are the same as those of FIG. 18. Accordingly, the descriptions are not repeated.

The advantages of the configuration in which the drive signal of the vibration-type actuator is transmitted via an optical fiber are described in more detail. To measure the pulse width of the pulse-width modulated signal output from the rotary encoder 52 and generate the pulse width modulated signal from a sine wave for driving the vibration-type actuator, the speed control unit 46 requires a counter having a reference clock in the range from several 10 to several 100 MHz. In addition, to operate a plurality of vibration-type actuators in conjunction with one another, a CPU that allows high-speed arithmetic operations for controlling the speeds may be needed. In recent years, such a control unit has been generally formed using FPGA. Noise caused by the high-frequency clocks is the greatest enemy of such MRI apparatuses. In particular, when the vibration-type actuator operates in the bore of the MRI apparatus, noise contamination in the vibration-type actuator needs to be avoided. Accordingly, by, as in the present exemplary embodiment, disposing the portion that operates with a high-frequency clock outside the magnetic shield room 1 and transmitting the signals to the inside of the magnetic shield room 1 using an optical fiber, generation of noise by the high-frequency clock in the magnetic shield room 1 can be advantageously blocked.

In addition, by connecting the drive signal and the encoder signal of the vibration-type actuator to a remote site using an optical fiber, the output signal output from a remote detection unit can be detected in real time. Even in a system that complicatedly controls the frequency, amplitude, phase difference, and driving waveform of a drive signal in order to control the state quantity, transmission delay is negligible. Accordingly, the waveform generating units can be disposed at a central location and, therefore, the configuration of the remote apparatus can be simplified. As a result, a low-cost system can be provided.

Furthermore, by using an optical fiber, the present exemplary embodiment can be used even in an electrically noisy environment, such as a factory. That is, the present exemplary embodiment is applicable to apparatuses that measure noise in a product. Accordingly, by integrating the control units of a plurality of the vibration-type actuators into a single FPGA and distributedly disposing the drive circuits of the vibration-type actuators, a low-cost application that performs highly accurate control using a plurality of vibration-type actuators can be provided.

Fourth Exemplary Embodiment

Figure 21:
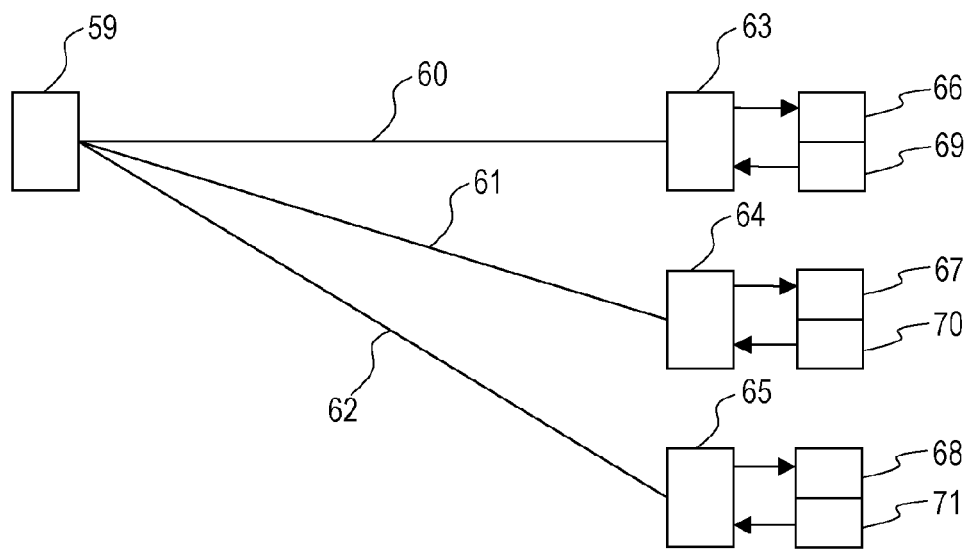
FIG. 21 is a schematic illustration of an exemplary system according to a fourth exemplary embodiment.

A fourth exemplary embodiment of the present disclosure is described next. FIG. 21 is a schematic illustration of an exemplary system for driving vibration-type actuators disposed on remote sites using a single control unit. A control unit 59 drives a plurality of vibration-type actuators disposed on a plurality of remote sites. Optical fibers 60, 61, and 62 transmit the driving waveform signals used for driving the vibration-type actuators in the form of optical signals. Drive circuits 63, 64, and 65 generate the drive voltages used for driving vibration-type actuators 66, 67, and 68 on the remote sites, respectively, for the control unit 59. Rotary encoders 69, 70, and 71 detect the rotational speeds of the vibration-type actuators 66, 67, and 68, respectively.

The optical fibers 60, 61, and 62 transmit signals obtained by performing ΔΣ modulation on the driving waveform signals of the vibration-type actuators 66, 67, and 68 to the drive circuits 63, 64, and 65, respectively. In addition, the optical fibers 60, 61, and 62 transmit the detection signals from the rotary encoders 69, 70, and 71 to the control unit 59. The transmission system using the optical fibers employs optical wavelength division multiplexing described in the first and third exemplary embodiments. According to the present exemplary embodiment, the plurality of signals are bi-directionally transmitted using a single optical fiber.

In each of the drive circuits 63, 64, and 65, the ΔΣ modulated driving waveform signal is converted into a smooth analog waveform using a low-pass filter and is amplified. Thereafter, the smooth analog waveform is applied to a corresponding one of the vibration-type actuators 66, 67, and 68 in the form of a drive voltage. Note that in general, the drive waveform of the vibration-type actuator is a sine wave. However, the present invention is not limited to a sine wave. For example, the present invention is applicable to a variety of cases, for example, the case in which the system combines saw-tooth waves, the case in which the system combines a plurality of frequencies, or the case in which the above-described two cases are switchable. Thus, the vibration-type actuator can be driven using a variety of waveforms.

As a system that drives a plurality of remote vibration-type actuators, the following two type of system can be provided: (1) a system in which control units are distributedly disposed and are connected over a network and instructions are sent from a central location and (2) a system in which a control unit is disposed at a central location and only simple drivers are distributedly disposed. Each of two types has its merits and demerits. In the system (1), it is difficult to operate the actuators in conjunction with one another, since variation in the processing time occurs due to various communication protocols and independent control performed by the control systems. In addition, since the number of control units increases, the total cost tends to increases. In contrast, in the system (2), by connecting the driving waveform signal of the vibration-type actuator and the detection signal output from the encoder to a remote site using the optical fiber, real-time control with minimum transmission delay can be provided even when complicated waveform control is performed. Accordingly, interaction among a plurality of actuators can be easily achieved.

In recent years, a large-scale high-power FPGA has been available at low cost. Thus, even an application that requires complicated waveform control or highly advanced arithmetic processing (e.g., model prediction) can be performed using a single FPGA that can execute a plurality of processes in parallel. By integrating a plurality of control units into a single FPGA, a low-cost system that performs highly accurate control can be provided. Note that while the present exemplary embodiment has been described with reference to a ΔΣ modulated drive waveform, the waveform is not limited thereto. For example, a simple square wave having a frequency that is the same as the alternating-current voltage may be employed.

According to the present invention, by transmitting the driving waveform signal used for driving the vibration-type actuator in the form of an optical signal, electromagnetic noise can be reduced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-135446 filed Jun. 15, 2012, which is hereby incorporated by reference herein in its entirety.

What is claimed is:

1. A measuring system for measuring a physical quantity related to one of an electromagnetic wave and a magnetic field comprising:
    a vibration-type actuator;
    a waveform generating unit configured to generate a driving waveform signal of the vibration-type actuator;
    an optical transmitter unit configured to receive the driving waveform signal and convert the driving waveform signal into an optical signal;
    an optical receiver unit configured to receive the optical signal and convert the optical signal into an alternating-current voltage signal; and
    a drive circuit configured to receive the alternating-current voltage signal and output a drive voltage to be applied to the vibration-type actuator,
    wherein the waveform generating unit and the optical transmitter unit are disposed outside a magnetic shield room, the optical receiver unit, the drive circuit, and the vibration-type actuator are disposed inside the magnetic shield room, and the optical signal is transmitted between the optical transmitter unit and the optical receiver unit.

2. The measuring system according to claim 1, further comprising:
    an optical combining unit; and
    an optical distribution unit,
    wherein the waveform generating unit generates a plurality of driving waveform signals, the optical transmitter unit converts each of the driving waveform signals into one of a plurality of optical signals having different wavelengths, the optical combining unit combines the optical signals, and the optical distribution unit separates the combined optical signal by wavelength into the optical signals.

3. The measuring system according to claim 1, further comprising:
    an optical waveguide unit configured to transfer the optical signal.

4. The measuring system according to claim 1, wherein the waveform generating unit outputs a pulse signal as the driving waveform signal.

5. The measuring system according to claim 4, wherein the waveform generating unit outputs, as the driving waveform signal, a pulse signal obtained by performing pulse modulation on a sine wave.

6. The measuring system according to claim 4, wherein the drive circuit includes a low-pass filter, and
    the drive circuit converts the pulse signal into an analog signal using the low-pass filter.

7. The measuring system according to claim 4, wherein the drive circuit includes a D/A converter, and
    the drive circuit converts the pulse signal into an analog signal using the D/A converter.

8. The measuring system according to claim 5, further comprising:
    a receiving unit configured to receive an electromagnetic wave from an examinee located inside of the magnetic shield room,
    wherein the waveform generating unit outputs a pulse signal obtained by performing one of pulse width modulation and pulse amplitude modulation on a sine wave as the driving waveform signal, and
    wherein a frequency that is an integer multiple of a modulation frequency of the pulse signal is not included in a Larmor frequency range.

9. A measuring system for measuring a physical quantity related to one of an electromagnetic wave and a magnetic field comprising:
    a vibration-type actuator;
    a waveform generating unit configured to generate a driving waveform signal of the vibration-type actuator;
    a first optical transmitter unit configured to receive the driving waveform signal and convert the driving waveform signal into a first optical signal;
    a first optical receiver unit configured to receive the first optical signal and convert the first optical signal into a first alternating-current voltage signal;
    a drive circuit configured to receive the first alternating-current voltage signal and apply the first alternating-current voltage signal to the vibration-type actuator;
    a detecting unit configured to detect a drive state of a driven member that is driven by the vibration-type actuator;
    a second optical transmitter unit configured to convert a detection signal output from the detecting unit into a second optical signal;
    a second optical receiver unit configured to receive the second optical signal and convert the second optical signal into a second alternating-current voltage signal; and
    a control unit configured to control at least one of a frequency, a phase, and an amplitude of the driving waveform signal on the basis of the second alternating-current voltage signal,
    wherein the waveform generating unit, the first optical transmitter unit, the second optical receiver unit, and the control unit are disposed outside a magnetic shield room, wherein the first optical receiver unit, the drive circuit, the vibration-type actuator, the detecting unit, and the second optical transmitter unit are disposed inside the magnetic shield room, and wherein the optical signal is transmitted between the first optical transmitter unit and the first optical receiver unit and between the second optical transmitter unit and the second optical receiver unit.

10. The measuring system according to claim 9, further comprising:
a first optical combining unit;
a first optical distribution unit;
a second optical combining unit; and
a second optical distribution unit,
wherein the waveform generating unit generates a plurality of the driving waveform signals, the first optical transmitter unit converts each of the driving waveform signals into one of a plurality of first optical signals having different wavelengths, the detecting unit outputs a plurality of detection signals, the second optical transmitter unit converts each of the detection signals into one of the second optical signals having different wavelengths, and
wherein the first optical combining unit combines the first optical signals, the first optical distribution unit separates the combined first optical signals by wavelength, the second optical combining unit combines the second optical signals, and the second optical distribution unit separates the combined second optical signals by wavelength.

11. The measuring system according to claim 9, further comprising:
an optical waveguide unit configured to transmit the first and second optical signals.

12. The measuring system according to claim 11, wherein the first and second optical signals are transmitted using the same optical waveguide unit.

13. The measuring system according to claim 9, wherein the waveform generating unit outputs a pulse signal as the driving waveform signal.

14. The measuring system according to claim 13, wherein the waveform generating unit outputs, as the driving waveform signal, a pulse signal obtained by performing pulse modulation on a sine wave.

15. The measuring system according to claim 13, wherein the drive circuit includes a low-pass filter, and
the drive circuit converts the pulse signal into an analog signal using the low-pass filter.

16. The measuring system according to claim 13, wherein the drive circuit includes a D/A converter, and
the drive circuit converts the pulse signal into an analog signal using the D/A converter.

17. The measuring system according to claim 9, wherein the detecting unit outputs, as the detection signal, a pulse signal obtained by performing pulse modulation on a sine wave, the second optical transmitter unit converts the pulse signal output from the detecting unit into the second optical signal,
the second optical receiver unit outputs a pulse signal as the second alternating-current voltage signal, and
the control unit obtains a waveform of a sine wave of the detection signal on the basis of the second alternating-current voltage signal and obtains the drive state.

18. The measuring system according to claim 14, further comprising:
a receiving unit configured to receive an electromagnetic wave from an examinee located inside of the magnetic shield room, wherein the waveform generating unit outputs, as the driving waveform signal, a pulse signal obtained by performing one of pulse width modulation and pulse amplitude modulation on a sine wave, and
wherein a frequency that is an integer multiple of a modulation frequency of the pulse signal is not included in a Larmor frequency range.

19. A system comprising:
a vibration-type actuator;
a waveform generating unit configured to generate a driving waveform signal transmitting a waveform of a drive voltage to be applied to the vibration-type actuator;
an optical transmitter unit configured to receive the driving waveform signal and convert the driving waveform signal into an optical signal;
an optical receiver unit configured to receive the optical signal and convert the optical signal into an alternating-current voltage signal; and
a drive circuit configured to receive the alternating-current voltage signal and output the drive voltage to be applied to the vibration-type actuator.

20. A system comprising:
a vibration-type actuator;
a waveform generating unit configured to generate a driving waveform signal transmitting a waveform of a drive voltage to be applied to the vibration-type actuator;
a first optical transmitter unit configured to receive the driving waveform signal and convert the driving waveform signal into a first optical signal;
a first optical receiver unit configured to receive the first optical signal and convert the first optical signal into a first alternating-current voltage signal;
a drive circuit configured to receive the first alternating-current voltage signal and apply the first alternating-current voltage signal to the vibration-type actuator;
a detecting unit configured to detect a drive state of a driven member that is driven by the vibration-type actuator;
a second optical transmitter unit configured to convert a detection signal output from the detecting unit into a second optical signal;
a second optical receiver unit configured to receive the second optical signal and convert the second optical signal into a second alternating-current voltage signal; and
a control unit configured to control at least one of a frequency, a phase, and an amplitude of the driving waveform signal on the basis of the second alternating-current voltage signal.

21. A measuring system for measuring a physical quantity related to one of an electromagnetic wave and a magnetic field comprising:
a vibration-type actuator;
a waveform generating unit configured to generate a driving waveform signal transmitting a waveform of a drive voltage to be applied to the vibration-type actuator;
an optical transmitter unit configured to receive the driving waveform signal and convert the driving waveform signal into an optical signal;
an optical receiver unit configured to receive the optical signal and convert the optical signal into an alternating-current voltage signal; and
a drive circuit configured to receive the alternating-current voltage signal and output the drive voltage to be applied to the vibration-type actuator,
wherein the waveform generating unit and the optical transmitter unit are disposed outside a magnetic shield room, the optical receiver unit, the drive circuit, and the vibration-type actuator are disposed inside the magnetic shield room, and the optical signal is transmitted between the optical transmitter unit and the optical receiver unit.

22. A measuring system for measuring a physical quantity related to one of an electromagnetic wave and a magnetic field comprising:
a vibration-type actuator;
a waveform generating unit configured to generate a driving waveform signal transmitting a waveform of a drive voltage to be applied to the vibration-type actuator;
a first optical transmitter unit configured to receive the driving waveform signal and convert the driving waveform signal into a first optical signal;
a first optical receiver unit configured to receive the first optical signal and convert the first optical signal into a first alternating-current voltage signal;
a drive circuit configured to receive the first alternating-current voltage signal and apply the first alternating-current voltage signal to the vibration-type actuator;
a detecting unit configured to detect a drive state of a driven member that is driven by the vibration-type actuator;
a second optical transmitter unit configured to convert a detection signal output from the detecting unit into a second optical signal;
a second optical receiver unit configured to receive the second optical signal and convert the second optical signal into a second alternating-current voltage signal; and
a control unit configured to control at least one of a frequency, a phase, and an amplitude of the driving waveform signal on the basis of the second alternating-current voltage signal,
wherein the waveform generating unit, the first optical transmitter unit, the second optical receiver unit, and the control unit are disposed outside a magnetic shield room,
wherein the first optical receiver unit, the drive circuit, the vibration-type actuator, the detecting unit, and the second optical transmitter unit are disposed inside the magnetic shield room, and
wherein the optical signal is transmitted between the first optical transmitter unit and the first optical receiver unit and between the second optical transmitter unit and the second optical receiver unit.

23. A system comprising:
a vibration-type actuator;
a waveform generating unit configured to generate a driving waveform signal transmitting a waveform of a drive voltage to be applied to the vibration-type actuator;
an optical transmitter unit configured to receive the driving waveform signal and convert the driving waveform signal into an optical signal;
an optical receiver unit configured to receive the optical signal and convert the optical signal into an alternating-current voltage signal; and
a drive circuit configured to receive the alternating-current voltage signal and output the drive voltage to be applied to the vibration-type actuator,
wherein the waveform generating unit and the optical transmitter unit are disposed outside a magnetic shield room, the optical receiver unit, the drive circuit, and the vibration-type actuator are disposed inside the magnetic shield room, and the optical signal is transmitted between the optical transmitter unit and the optical receiver unit.

24. A system comprising:
a vibration-type actuator;
a waveform generating unit configured to generate a driving waveform signal transmitting a waveform of a drive voltage to be applied to the vibration-type actuator;
a first optical transmitter unit configured to receive the driving waveform signal and convert the driving waveform signal into a first optical signal;
a first optical receiver unit configured to receive the first optical signal and convert the first optical signal into a first alternating-current voltage signal;
a drive circuit configured to receive the first alternating-current voltage signal and apply the first alternating-current voltage signal to the vibration-type actuator;
a detecting unit configured to detect a drive state of a driven member that is driven by the vibration-type actuator;
a second optical transmitter unit configured to convert a detection signal output from the detecting unit into a second optical signal;
a second optical receiver unit configured to receive the second optical signal and convert the second optical signal into a second alternating-current voltage signal; and
a control unit configured to control at least one of a frequency, a phase, and an amplitude of the driving waveform signal on the basis of the second alternating-current voltage signal,
wherein the waveform generating unit, the first optical transmitter unit, the second optical receiver unit, and the control unit are disposed outside a magnetic shield room,
wherein the first optical receiver unit, the drive circuit, the vibration-type actuator, the detecting unit, and the second optical transmitter unit are disposed inside the magnetic shield room, and
wherein the optical signal is transmitted between the first optical transmitter unit and the first optical receiver unit and between the second optical transmitter unit and the second optical receiver unit.

* * * * *